(12) United States Patent
Eller

(10) Patent No.: US 9,980,813 B2
(45) Date of Patent: May 29, 2018

(54) SELECTIVE FLUID BARRIER VALVE DEVICE AND METHOD OF TREATMENT

(71) Applicant: Cook Medical Technologies LLC, Bloomington, IN (US)

(72) Inventor: Derek Eller, Orient, OH (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 402 days.

(21) Appl. No.: 14/689,734

(22) Filed: Apr. 17, 2015

(65) Prior Publication Data

US 2015/0305859 A1 Oct. 29, 2015

Related U.S. Application Data

(60) Provisional application No. 61/985,134, filed on Apr. 28, 2014.

(51) Int. Cl.
*A61M 39/00* (2006.01)
*A61F 2/24* (2006.01)
(Continued)

(52) U.S. Cl.
CPC .............. *A61F 2/24* (2013.01); *A61F 2/2469* (2013.01); *A61M 39/0613* (2013.01);
(Continued)

(58) Field of Classification Search
CPC ........ A61M 39/288; F16K 7/06; F16K 7/061; F16K 7/063; F16K 7/08
(Continued)

(56) References Cited

U.S. PATENT DOCUMENTS 2,434,835 A * 1/1948 Colley ...................... F16K 7/06
138/45
3,383,131 A * 5/1968 Rosfelder ............... E21B 25/06
175/240

(Continued)

FOREIGN PATENT DOCUMENTS

| WO | WO03048616 | 6/2003 |
| WO | WO2007016122 | 2/2007 |
| WO | WO2007035471 | 3/2007 |

OTHER PUBLICATIONS

European Patent Office, "Extended European Search Report," for Int. App. No. 15165062.9, dated Sep. 24, 2015, pp. 1-7.
(Continued)

*Primary Examiner* — Kami A Bosworth
*Assistant Examiner* — William Carpenter
(74) *Attorney, Agent, or Firm* — Buchanan Van Tuinen LLC

(57) ABSTRACT

Selective fluid barrier valve devices and methods of treatment are described herein. An embodiment of a selective fluid barrier valve device comprises a housing, an actuator, a sleeve, a wire member, and a connector. The sleeve defines a passageway that extends through the sleeve. The actuator is moveable between a first position and a second position. When the actuator is in the first position, the sleeve is in a first configuration such that fluid can pass through the passageway defined by the sleeve. When the actuator is in a second position, the sleeve is in a second configuration such that fluid is prevented from passing through the passageway defined by the sleeve.

4 Claims, 11 Drawing Sheets

(51) Int. Cl.
*A61M 39/06* (2006.01)
*A61M 39/22* (2006.01)
*A61M 39/28* (2006.01)
*F16K 7/06* (2006.01)

(52) U.S. Cl.
CPC .......... *A61M 39/22* (2013.01); *A61M 39/288* (2013.01); *F16K 7/06* (2013.01)

(58) Field of Classification Search
USPC .......................................... 251/4, 9, 10, 294
See application file for complete search history.

(56) References Cited

U.S. PATENT DOCUMENTS

| | | | |
|---|---|---|---|
| 3,383,161 A * | 5/1968 | Fukunaga | C08K 5/20 8/601 |
| 3,419,008 A | 12/1968 | Plishner | |
| 3,675,656 A | 7/1972 | Hakim | |
| 3,699,957 A | 10/1972 | Robinson | |
| 3,730,186 A | 5/1973 | Edmunds, Jr. et al. | |
| 3,744,063 A | 7/1973 | McWhorter et al. | |
| 3,750,194 A | 8/1973 | Summers | |
| 3,817,237 A | 6/1974 | Bolduc | |
| 3,926,175 A | 12/1975 | Allen et al. | |
| 3,939,821 A | 2/1976 | Roth | |
| 4,080,958 A | 3/1978 | Bregman et al. | |
| 4,092,010 A | 5/1978 | Carlson | |
| 4,195,810 A * | 4/1980 | Lavin | F16K 7/07 251/5 |
| 4,245,358 A | 1/1981 | Moasser | |
| 4,256,093 A | 3/1981 | Helms et al. | |
| 4,408,597 A | 10/1983 | Tenney, Jr. | |
| 4,412,669 A * | 11/1983 | Hanyu | F16K 7/06 251/212 |
| 4,417,360 A | 11/1983 | Moasser | |
| 4,523,737 A * | 6/1985 | Wentworth | F16K 7/08 251/213 |
| 4,551,862 A | 11/1985 | Haber | |
| 4,552,128 A | 11/1985 | Haber | |
| 4,828,544 A | 5/1989 | Lane et al. | |
| 4,875,897 A | 10/1989 | Lee | |
| 4,958,630 A | 9/1990 | Rosenbluth et al. | |
| 4,982,731 A | 1/1991 | Lue et al. | |
| 5,167,637 A | 12/1992 | Okada et al. | |
| 5,207,409 A | 5/1993 | Riikonen | |
| 5,257,973 A | 11/1993 | Villasuso | |
| 5,269,772 A | 12/1993 | Wilk | |
| 5,354,271 A | 10/1994 | Voda | |
| 5,366,506 A | 11/1994 | Davis | |
| 5,383,896 A | 1/1995 | Gershony et al. | |
| 5,453,079 A | 9/1995 | Schwaninger | |
| 5,762,599 A | 6/1998 | Sohn | |
| 5,797,879 A | 8/1998 | DeCampli | |
| 5,814,026 A | 9/1998 | Yoon | |
| 5,891,113 A | 4/1999 | Quinn | |
| 5,919,183 A | 7/1999 | Field | |
| 6,099,506 A | 8/2000 | Macoviak et al. | |
| 6,102,361 A | 8/2000 | Riikonen | |
| 6,162,238 A | 12/2000 | Kaplan et al. | |
| 6,217,555 B1 | 4/2001 | Hart et al. | |
| 6,352,520 B1 | 3/2002 | Miyazaki | |
| 6,352,521 B1 | 3/2002 | Prosl | |
| 6,409,656 B1 | 6/2002 | Sangouard | |
| 6,547,801 B1 | 4/2003 | Dargent et al. | |
| 6,616,624 B1 | 9/2003 | Kieval | |
| 6,623,426 B2 | 9/2003 | Bonadio et al. | |
| 7,025,741 B2 | 4/2006 | Cull | |
| 7,367,938 B2 | 5/2008 | Forsell | |
| 7,479,105 B2 | 1/2009 | Matsumura | |
| 7,648,120 B1 | 1/2010 | Kota et al. | |
| 7,736,328 B2 | 6/2010 | Childers et al. | |
| 7,762,980 B2 | 7/2010 | Gertner | |
| 7,762,999 B2 | 7/2010 | Byrum | |
| 8,096,989 B2 | 1/2012 | Buffard et al. | |
| 8,114,044 B2 | 2/2012 | Cull | |
| 8,152,711 B2 | 4/2012 | Gross | |
| 8,206,294 B2 | 6/2012 | Widenhouse et al. | |
| 8,226,592 B2 | 7/2012 | Brenneman et al. | |
| 8,506,517 B2 | 8/2013 | Stergiopulos | |
| 8,690,834 B2 | 4/2014 | Koehler | |
| 8,728,105 B2 | 5/2014 | Aguirre | |
| 9,440,059 B2 * | 9/2016 | Moore | A61M 39/0613 |
| 2003/0116731 A1 * | 6/2003 | Hartley | A61M 39/0613 251/7 |
| 2004/0000122 A1 | 1/2004 | Sterner et al. | |
| 2004/0015159 A1 | 1/2004 | Slater et al. | |
| 2004/0064100 A1 | 4/2004 | Smith | |
| 2004/0167559 A1 | 8/2004 | Taylor et al. | |
| 2007/0027460 A1 | 2/2007 | Case et al. | |
| 2007/0078395 A1 | 4/2007 | Valaie | |
| 2007/0106262 A1 | 5/2007 | Becker et al. | |
| 2009/0326468 A1 | 12/2009 | Blier | |
| 2010/0127194 A1 | 5/2010 | Landry | |
| 2012/0271116 A1 | 10/2012 | Koehler | |
| 2012/0310166 A1 | 12/2012 | Huff | |

OTHER PUBLICATIONS

Gore & Associates, Inc, Product Information Sheet, Gore DrySeal Valve, 2010.
Medtronic Neurosurgery, Pediatric Shunt Case using a Strata II Valve with William Louden MD, YouTube.com, published Jul. 5, 2013.
Medtronic, Strata Valves, http://www.medtronic.com/patients/hydocephalus/device/our-shunts/strata-valves/index.htm, last updated Oct. 8, 2012, accessed Sep. 11, 2014.
United States Patent and Trademark Office, Final Office Action for U.S. Appl. No. 13/092,410, first named inventor: Cleve Koehler, dated Nov. 6, 2013, pp. 1-41.
United States Patent and Trademark Office, Non-final Office Action for U.S. Appl. No. 13/092,410, first named inventor: Cleve Koehler, dated Jun. 21, 2013, pp. 1-31.

\* cited by examiner

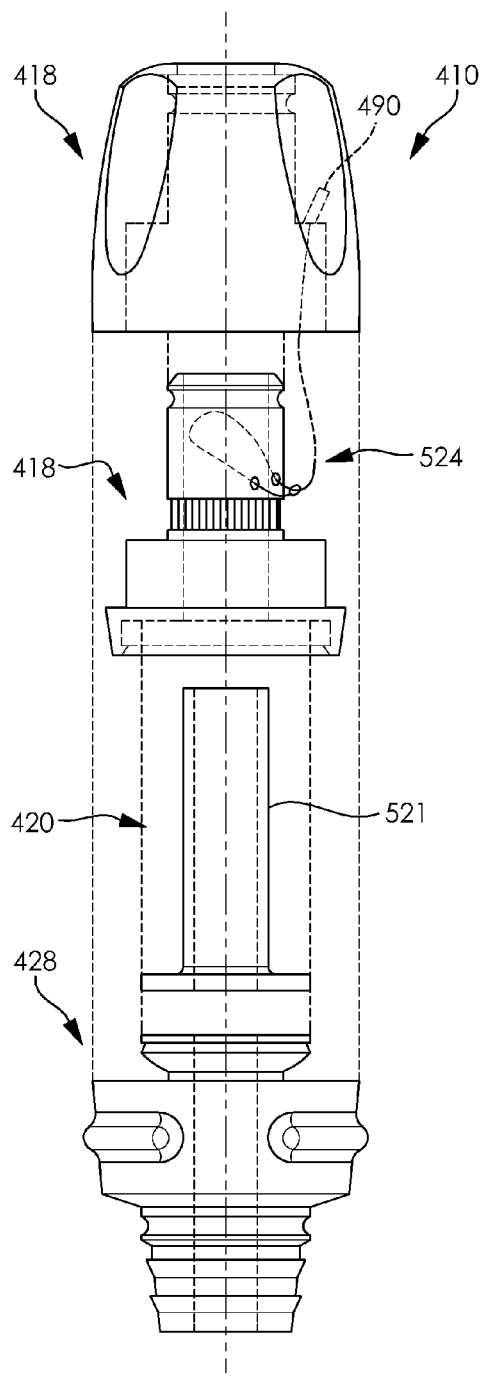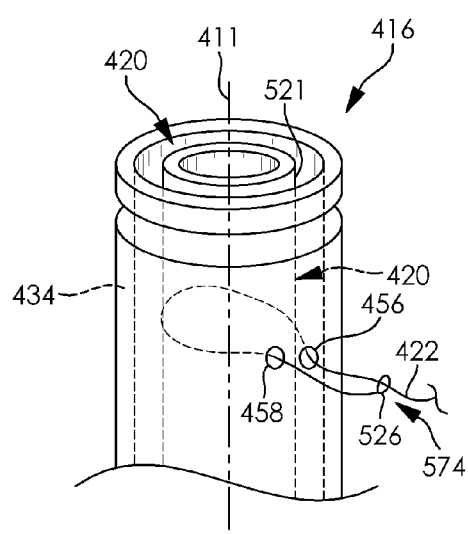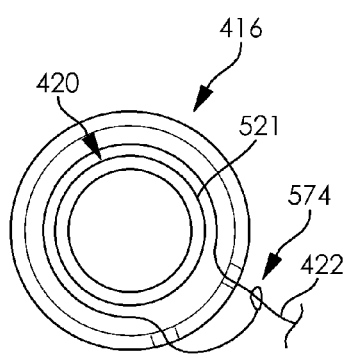
FIG. 15
FIG. 16
FIG. 17

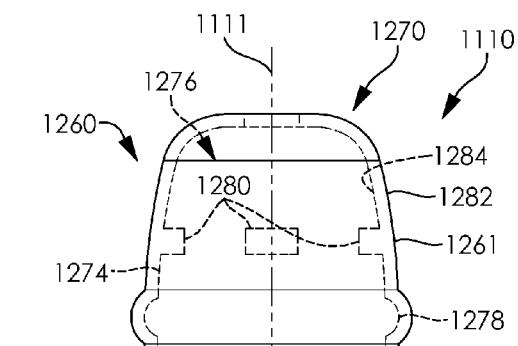
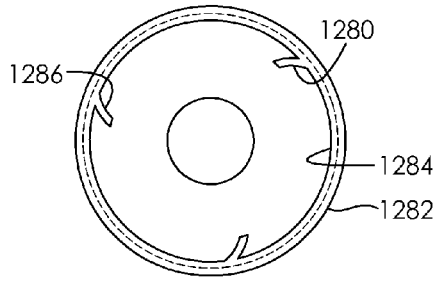
FIG. 25
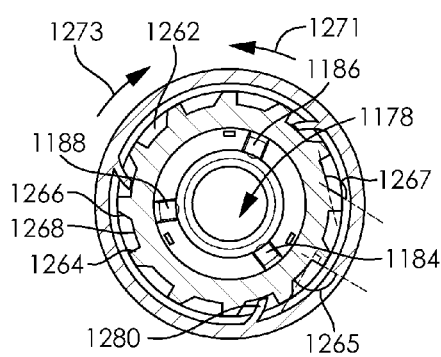
FIG. 26
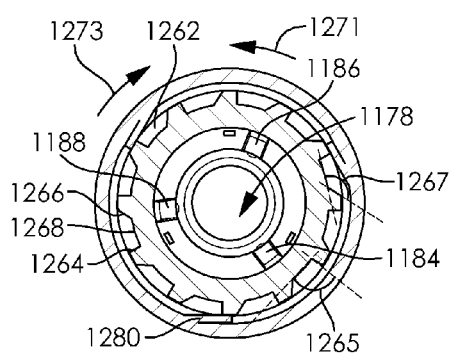
FIG. 27
FIG. 24

SELECTIVE FLUID BARRIER VALVE DEVICE AND METHOD OF TREATMENT

RELATED APPLICATION

This application claims the benefit of U.S. Provisional Application No. 61/985,134, filed Apr. 28, 2014. The disclosure of this related application is hereby incorporated into this disclosure in its entirety.

FIELD

The disclosure relates generally to the field of medical devices. Particular embodiments are related to selective fluid barrier valve devices and methods of treatment using a selective fluid barrier valve device.

BACKGROUND

A variety of procedures have been developed that require the percutaneous insertion of one or more interventional devices into a bodily passage, such as a portion of the vascular system. Such procedures include, for example, percutaneous transluminal coronary angioplasty (PTCA), X-ray angiographic procedures, and the like. The interventional devices intended for use in such procedures may be introduced into the bodily passage using a variety of known techniques. For example, an introducer can be advanced into a bodily passageway over a previously placed guide wire and used as a conduit for the insertion of an interventional device into the bodily passage.

In many cases, an introducer will include one or more valves for inhibiting leakage of bodily fluids, such as blood, through the introducer as an interventional device is inserted through or withdrawn from the introducer. In some cases, valves that include an elastomeric component and define a small slit are used to minimize fluid leakage during these exchanges. These valves are dependent upon the ability of the elastomeric component to seal around an interventional device to close any gaps created upon insertion or withdrawal of the device through the valve. Generally, these valves can only accommodate interventional devices that have outside diameters that fall within a small range. In addition, during the performance of a procedure, a user may be required to hold an interventional device disposed through a valve stationary to avoid slippage and to increase the performance of the valve.

Therefore, there is a need for improved fluid barrier valve devices and methods of treatment using a fluid barrier valve device.

BRIEF SUMMARY OF SELECTED EXAMPLE EMBODIMENTS

An example embodiment of a selective fluid barrier valve device that has a lengthwise axis and comprises a housing, an actuator, a sleeve, and a first wire member. The housing has a housing proximal end, a housing distal end, and a housing body that defines a housing passageway and a first opening. The housing passageway extends through the housing. The first opening extends through the housing body and provides access to the housing passageway. The actuator is moveably attached to the housing and is moveable between a first position and a second position. The sleeve is disposed within the housing passageway and has a sleeve proximal end, a sleeve distal end, and a sleeve body that defines a sleeve passageway that extends through the sleeve. The sleeve is moveable between a first configuration in which the sleeve passageway is open such that fluid can pass through the sleeve passageway and a second configuration in which the sleeve passageway is closed and prevents fluid from passing through the sleeve passageway. The first wire member has a first wire member first end attached to the housing and a first wire member second end attached to the actuator. The first wire member extends between the housing and the sleeve and through the first opening defined by the housing. The sleeve is in the first configuration and the sleeve proximal end is disposed a first distance from the housing proximal end when the actuator is in the first position. The sleeve is in the second configuration and the sleeve proximal end is disposed a second distance from the housing proximal end when the actuator is in the second position. The second distance is different than the first distance.

An example method of treatment using a selective fluid barrier valve device comprises the steps of: attaching a selective fluid barrier valve device to a first medical device that has a proximal end, a distal end, and a body that defines a lumen that extends from the proximal end to the distal end, the selective fluid barrier valve device has a lengthwise axis and comprises a housing, an actuator, a sleeve, and a first wire member; inserting the first medical device into a bodily passage such that the distal end of the first medical device is disposed within the bodily passage; inserting a second medical device that has a proximal end and a distal end through the selective fluid barrier valve device and the first medical device such that the distal end of the second medical device is disposed within the bodily passage; navigating the distal end of the second medical device to a point of treatment within the bodily passage; moving the actuator of the selective fluid barrier valve device from the first position to the second position; performing treatment using the second medical device; moving the actuator of the selective fluid barrier valve device from the second position to the first position; withdrawing the second medical device from the bodily passage, the first medical device, and the selective fluid barrier valve device; and withdrawing the first medical device from the bodily passage.

DESCRIPTION OF FIGURES

FIG. 15 is an exploded view of another example selective fluid barrier valve device.

FIG. 16 is a partial perspective view of the selective fluid barrier valve device illustrated in FIG. 15. The selective fluid barrier valve device is illustrated in a first configuration. Each of the actuator and the connector has been omitted for clarity.

FIG. 17 is an end view of the proximal end of the selective fluid barrier valve device illustrated in FIG. 16.

FIG. 24 is an exploded view of another example selective fluid barrier valve device.

FIG. 25 is an end view of the distal end of the second actuator of the selective fluid barrier valve device illustrated in FIG. 24.

FIG. 26 is an end view of the distal end of the first actuator and the second actuator of the selective fluid barrier valve device illustrated in FIG. 24. Each projection of the plurality of projections of the second actuator is in a first configuration.

FIG. 27 is an end view of the distal end of the first actuator and the second actuator of the selective fluid barrier valve device illustrated in FIG. 24. Each projection of the plurality of projections of the second actuator is in a second configuration.

DESCRIPTION OF EMBODIMENTS

Figure 1:
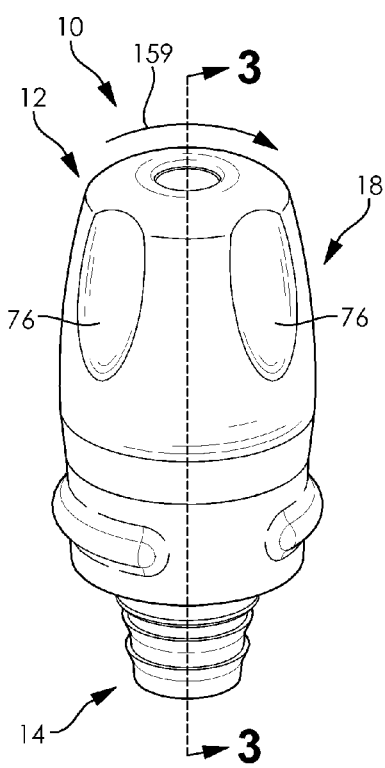
FIG. 1 is a perspective view of an example selective fluid barrier valve device.

The following detailed description and the appended drawings describe and illustrate various example embodiments of selective fluid barrier valve devices and methods of treatment. The description and illustration of these examples are provided to enable one skilled in the art to make and use a selective fluid barrier valve device and to practice a method of treatment using a selective fluid barrier valve device. They are not intended to limit the scope of the claims in any manner.

The use of "e.g.," "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present or occur, and that the description includes instances where said element, event, feature, or circumstance occurs and instances where it does not. The term "attached" refers to the fixed, releasable, or integrated association of two or more elements and/or devices. Thus, the term "attached" includes releasably attaching and fixedly attaching two or more elements and/or devices. As used herein, the terms "proximal" and "distal" are used to describe opposing axial ends of the particular element or feature being described. The term "diameter" refers to the length of a straight line passing from side to side through the center of a body, element, or feature, and does not impart any structural configuration on the body, element, or feature. The term "circumference" refers to the distance around the exterior surface of a body, element, or feature, and does not impart any structural configuration on the body, elements, or feature. The use of "bodily passage" or "body passage" refers to any passage within the body of an animal, including humans, and includes elongate passages, arteries, and veins.

FIGS. 1, 2, 3, 4, 5, 6, 7, 8A, 8B, 8C, 9A, 9B, 9C, 10A, 10B, and 10C illustrate an embodiment of a selective fluid barrier valve device 10 that has a lengthwise axis 11, a proximal end 12, a distal end 14, a housing 16, an actuator 18, a sleeve 20, a first wire member 22, a second wire member 24, a third wire member 26, and a connector 28. The selective fluid barrier valve device 10 is moveable between a first configuration and a second configuration, as described in more detail herein. In the first configuration, fluid can pass through the selective fluid barrier valve device 10. In the second configuration, fluid is prevented from passing through the selective fluid barrier valve device 10.

Figure 2:
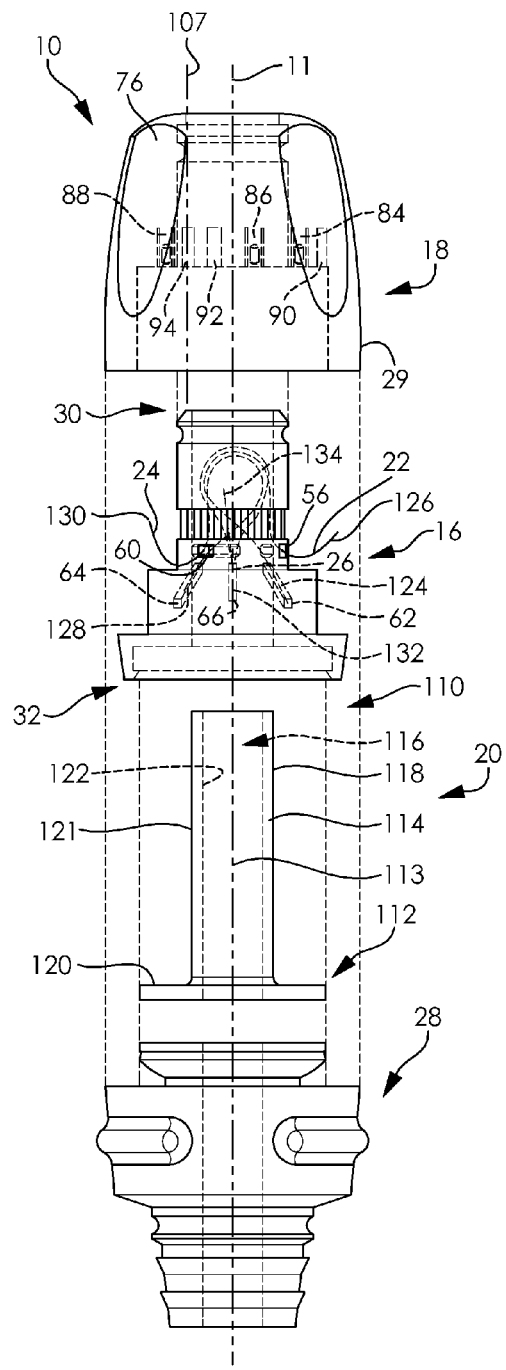
FIG. 2 is an exploded view of the selective fluid barrier valve device illustrated in FIG. 1.
Figure 3:
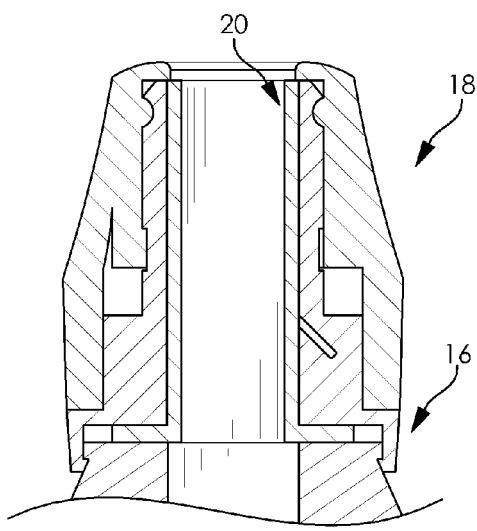
FIG. 3 is a partial cross-sectional view of the selective fluid barrier valve device illustrated in FIG. 1, taken along line 3-3. The selective fluid barrier valve device is illustrated in a first configuration. Each of the first wire member, the second wire member, and the third wire member has been omitted for clarity.
Figure 4:
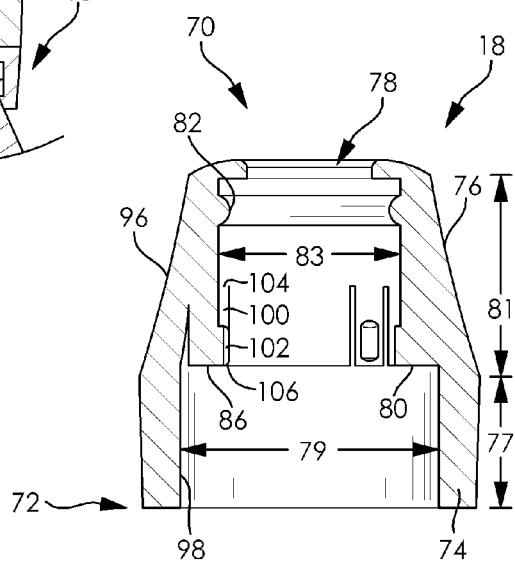
FIG. 4 is a sectional view of the actuator of the selective fluid barrier valve device illustrated in FIG. 1 taken along the lengthwise axis of the actuator.
Figure 5:
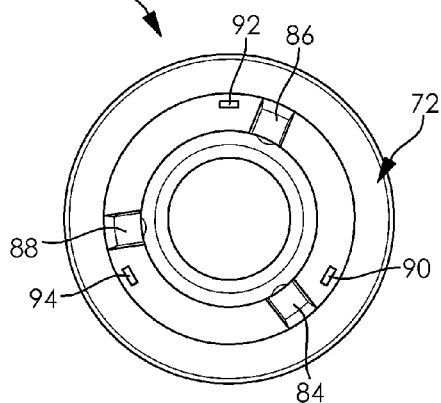
FIG. 5 is an end view of the distal end of the actuator of the selective fluid barrier valve device illustrated in FIG. 1.
Figure 6:
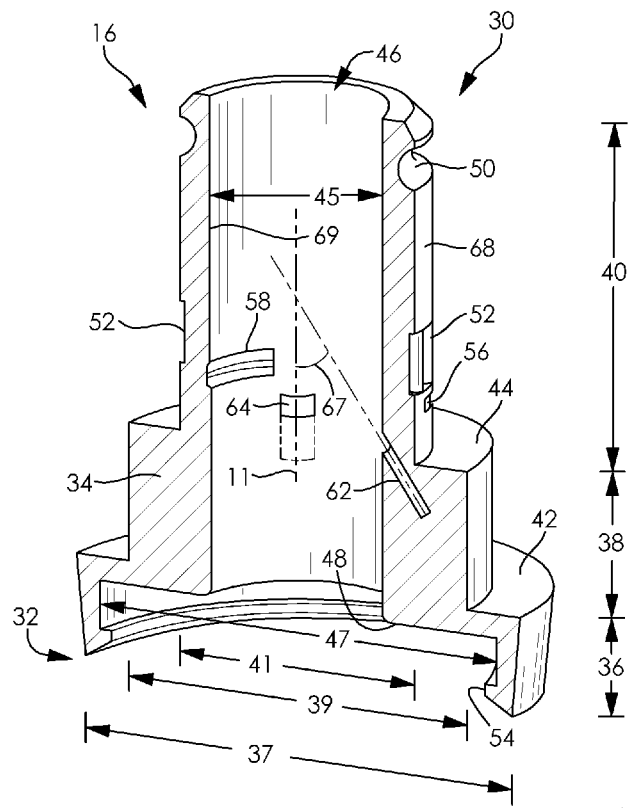
FIG. 6 is a perspective sectional view of the housing of the selective fluid barrier valve device illustrated in FIG. 1 taken along the lengthwise axis of the housing.

In the embodiment illustrated, and as shown in FIGS. 2 and 6, the housing 16 has a tapered proximal end 30, a distal end 32, and a housing body 34 that defines a first portion 36, a second portion 38, a third portion 40, a first shoulder 42, a second shoulder 44, a passageway 46, a third shoulder 48, a groove 50, a plurality of recesses 52, a protuberance 54, a first opening 56, a second opening 58, a third opening 60, a first cavity 62, a second cavity 64, a third cavity 66, an outer surface 68, and an inner surface 69.

The first portion 36 of the housing 16 extends from the distal end 32 toward the proximal end 30 of the housing 16 and to the second portion 38. The second portion 38 of the housing 16 extends from the first portion 36 toward the proximal end 30 of the housing 16 to the third portion 40. The third portion 40 extends from the second portion 38 to the proximal end 30 of the housing 16. Thus, the second portion 38 is disposed between the first portion 36 and the third portion 40. The first portion 36 has a first outside diameter 37, the second portion 38 has a second outside diameter 39, and the third portion 40 has a third outside diameter 41. The first outside diameter 37 is greater than the second outside diameter 39 creating the first shoulder 42. The second outside diameter 39 is greater than the third outside diameter 41 creating the second shoulder 44.

The passageway 46 extends through the housing 16 from the proximal end 30 to the distal end 32 of the housing 16. The passageway 46 has a first inside diameter 45 at the proximal end 30 of the housing 16 and a second inside diameter 47 at the distal end 32 of the housing 16. The first inside diameter 45 is less than the second inside diameter 47 creating the third shoulder 48 within the passageway 46. The passageway 46 is sized and configured to receive a portion of the connector 28 and the sleeve 20, as described in more detail herein.

The groove 50 is defined on the third portion 40 of the housing 16 and extends into the housing body 34 toward the passageway 46 and around the entire circumference of the outer surface 68 of the housing 16. However, alternative embodiments can include a groove that extends about a portion of the circumference of the outer surface of a housing. The groove 50 is sized and configured to receive a portion of the actuator 18 (e.g., protuberance 82). The tapered proximal end 30 of the housing 16 is sized and configured to be advanced proximally over the protuberance 82 defined by the actuator 18 such that the protuberance 82 can be disposed within the groove 50. The groove 50 and the protuberance 82 cooperatively provide a mechanism for moveably attaching the actuator 18 to the housing 16 (e.g., snap fit configuration).

The plurality of recesses 52 is defined on the third portion 40 of the housing 16 and is disposed around the entire circumference of the outer surface 68 of the housing 16. However, alternative embodiments can include a recess, or a plurality of recesses, that extend around a portion of the circumference of a housing. Each recess of the plurality of recesses 52 is sized and configured to receive a portion of a rib (e.g., first rib 84, second rib 86, third rib 88) defined by the actuator 18, as described below. The plurality of recesses 52 provides a mechanism for maintaining the position of the actuator 18 on the housing 16 (e.g., first position, second position).

While a plurality of recesses 52 has been illustrated as defined on the third portion 40 of the housing 16, a selective fluid barrier valve device can include any suitable number of recesses defined at any suitable location on a housing. Skilled artisans will be able to select a suitable number of recesses to define on a housing and a suitable location to position each recess according to a particular embodiment based on various considerations, including the structural arrangement of an actuator of an embodiment. Example number of recesses considered suitable to include on a housing include one, at least one, two, a plurality, three, four, five, six, and any other number considered suitable for a particular embodiment. Example locations considered suitable to position a recess, or a plurality of recesses, on a housing include on the first portion of the housing, on the second portion of the housing, and/or on the third portion of the housing.

The protuberance 54 is defined within the passageway 46 on the first portion 36 of the housing 16 and extends toward the lengthwise axis 11 of the selective fluid barrier valve device 10. The protuberance 54 extends around the entire circumference of the inner surface 69 of the housing 16 and is sized and configured to be received by the groove 156 define by the connector 28, as described in more detail herein. However, alternative embodiments can include a housing that defines a protuberance that extends around a portion of the circumference of the inner surface of the housing. The protuberance 54 provides a mechanism for releasably attaching the housing 16 to the connector 28 (e.g., snap fit configuration).

Each of the first opening 56, the second opening 58, and the third opening 60 extends through the housing body 34 and provides access to the passageway 46. Each of the openings 56, 58, 60 is sized and configured to receive a portion of a wire member (e.g., first wire member 22, second wire member 24, third wire member 26). The first opening 56 is disposed a first distance from the second opening 58, the second opening 58 is disposed a second distance from the third opening 60, and the third opening 60 is disposed a third distance from the first opening 56. In the illustrated embodiment, the first distance, the second distance, and the third distance are equal to one another. However, alternative embodiments can include a first opening that is disposed a first distance from a second opening, the second opening is disposed a second distance from a third opening, and the third opening is disposed a third distance from the first opening such that the first distance is different than the second distance and the second distance is the same as, or different than, the third distance. Thus, alternative embodiments can include a plurality of openings such that a first distance between a first opening and a second opening is different than a second distance between the second opening and a third opening, or between the second opening and the first opening.

In the illustrated embodiment, each of the openings 56, 58, 60 is elongated such that the opening has a length around the circumference of the housing 16 that is greater than the height of the opening. This provides a mechanism for moving the actuator 18 from the first position to the second position such that each of the wire members 56, 58, 60 can be moved within its respective opening and from its first configuration to its second configuration, as described in more detail herein.

Each of the first cavity 62, the second cavity 64, and the third cavity 66 extends into the housing body 34 from the inner surface 69 and is sized and configured to receive a portion of a wire member (e.g., first wire member 22, second wire member 24, third wire member 26). The first cavity 62 is disposed a first distance from the second cavity 64, the second cavity 64 is disposed a second distance from the third cavity 66, and the third cavity 66 is disposed a third distance from the first cavity 62. In the illustrated embodiment, the first distance, the second distance, and the third distance are equal to one another and each of the first distance, the second distance, and the third distance is measured along the inner surface 69 of the housing 16. However, alternative embodiments can include a first cavity that is disposed a first distance from a second cavity, the second cavity is disposed a second distance from a third cavity, and the third cavity is disposed a third distance from the first cavity such that the first distance is different than the second distance and the second distance is the same as, or different than, the third distance. Thus, alternative embodiments can include a plurality of cavities such that a first distance between a first cavity and a second cavity is different than a second distance between the second cavity and a third cavity, or between the second cavity and the first cavity.

In the illustrated embodiment, each of the cavities 62, 64, 66 extends into the housing body 34 from an opening defined on the inner surface 69 of the housing 16 toward the outer surface 68 and toward the distal end 32 of the housing 16. The opening of each of the first cavity 62, second cavity 64, and the third cavity 66 is disposed on a plane that is disposed orthogonal to the lengthwise axis 11 of the selective fluid barrier valve device 10. However, alternative embodiments can include a housing that defines a plurality of cavities such that at least one, or more than one, cavity is defined on a first plane that is disposed orthogonal to the lengthwise axis of the selective fluid barrier valve device and at lease one, or more than one, cavity is disposed on a second plane that is different than the first plane and is disposed orthogonal to the lengthwise axis of the selective fluid barrier valve device. Each of the cavities 62, 64, 66 has a lengthwise axis that extends at an angle 67 relative to the lengthwise axis 11 of the selective fluid barrier valve device 10 (i.e., a plane that contains the lengthwise axis 11 of the selective fluid barrier valve device 10). In the illustrated embodiment, the angle 67 is oblique and equal to 35 degrees. However, alternative embodiments can include a cavity disposed at any suitable angle relative to a lengthwise axis of a selective fluid barrier valve device (i.e., a plane that contains the lengthwise axis of a selective fluid barrier valve device), such as angles that are equal to, substantially equal to, or about 35 degrees, angles that are oblique, angles that are obtuse, angles that are acute, and any other angle considered suitable for a particular embodiment. Alternatively, a cavity can be disposed parallel to the lengthwise axis of a selective fluid barrier valve device. Any angle that is capable of securing an end of a wire member and does not impart kinking or excessive stress on the wire member is considered suitable.

While the housing 16 has been illustrated as having a particular structural arrangement, a housing can have any suitable structural arrangement and skilled artisans will be able to select a suitable structural arrangement for a housing according to a particular embodiment based on various considerations, including the number of wire members included in a selective fluid barrier valve device. For example, while a groove has been illustrated, a housing body can define any suitable structure capable of providing a mechanism to moveably attach an actuator to a housing, such as a protuberance that is received by a groove defined by the actuator. While the housing 16 has been illustrated as having a tapered proximal end 30, alternative embodiments can include a housing that does not define a tapered proximal end. While the housing body 34 has been illustrated as defining a plurality of openings 56, 58, 60 and a plurality of cavities 62, 64, 66, a housing body can define any suitable number of openings and/or cavities, such as one, at least one, two, a plurality, three, four, five, six, and any other number considered suitable for a particular embodiment. The number of openings and cavities defined by a housing can be based on the number of wire members included in a selective fluid barrier valve device.

In the illustrated embodiment, and as shown in FIGS. 1, 2, 4, and 5, the actuator 18 has a proximal end 70, a distal end 72, and an actuator body 74 that defines a plurality of recesses 76, a passageway 78, a shoulder 80, a protuberance 82, a first rib 84, a second rib 86, a third rib 88, a first cavity 90, a second cavity 92, a third cavity 94, an outer surface 96, and an inner surface 98. The actuator 18 is movably attached to the housing 16 and is moveable between a first position and a second position.

In the illustrated embodiment, the actuator 18 is a rotatable member 29 that can be rotated on the housing 16 around the lengthwise axis 11 of the selective fluid barrier valve device 10. However, while a rotatable member 29 has been illustrated, a selective fluid barrier valve device can include any suitable actuator capable of moving the selective fluid barrier valve device between a first configuration and a second configuration. Skilled artisans will be able to select a suitable actuator to include on a selective fluid barrier valve device according to a particular embodiment based on various considerations, including the number of wire members included in the selective fluid barrier valve device and/or the structural arrangement of the housing. Example actuators considered suitable to include on a selective fluid barrier valve device include rotatable actuators, linear actuators, slidable actuators, pivotable actuators, levers, and any other actuator considered suitable for a particular embodiment.

Each recess of the plurality of recesses 76 extends into the actuator body 74 from the outer surface 96 toward the inner surface 98 and is sized and configured to receive a portion of a finger of a user. Each recess of the plurality of recesses 76 provides an ergonomical structure that can be used to rotate the actuator 18 on the housing 16. Optionally, the plurality of recesses 76 can be omitted from the actuator 18.

The passageway 78 extends through the actuator 18 from the proximal end 70 to the distal end 72 of the actuator 18. The passageway 78 has a first portion 77 and a second portion 81. The first portion 77 extends from the distal end 72 of the actuator 18 toward the proximal end 70 of the actuator 18. The second portion 81 extends from the first portion 77 to the proximal end 70 of the actuator 18. The first portion 77 has a first inside diameter 79 and the second portion 81 and has a second inside diameter 83. The first inside diameter 79 is greater than the second inside diameter 83 creating the shoulder 80 within the passageway 78. The passageway 78 is sized and configured to receive a portion of the housing 16. The first portion 77 is sized and configured to receive the second portion 38 of the housing 16 and the second portion 81 is sized and configured to receive the third portion 40 of the housing 16.

The protuberance 82 extends from the inner surface 98 into the passageway 78 and around the entire circumference of the inner surface 98. However, alternative embodiments can include a protuberance that extends around a portion of the inner surface of the passageway defined by an actuator. The protuberance 82 is sized and configured to be received by the groove 50 defined by the housing 16 such that when the protuberance 82 is disposed within the groove 50 the actuator 18 is moveably attached to the housing 16 (e.g., a snap fit attachment between the housing 16 and the actuator 18 is achieved).

Each of the first rib 84, the second rib 86, and third rib 88 has a shaft 100 and a protuberance 102 and is moveable within the passageway 78. The shaft 100 has a first end 104 attached to the actuator body 74 and a second end 106 that is free of attachment to the actuator body 74. The protuberance 102 extends from the shaft 100 and toward the lengthwise axis 11 of the selective fluid barrier valve device 10. The protuberance 102 is sized and configured to be received by a recess of the plurality of recesses 52 defined by the housing 16.

This structural arrangement provides a mechanism for moving the actuator 18 between its first position and its second position on the housing 16 and maintaining the position of the actuator 18 when no outside force is being applied to the actuator 18. In the first position, each of the ribs 84, 86, 88 is disposed in a recess of the plurality of recesses 52. For example, the first rib 84 is disposed in a first recess of the plurality of recesses 52, the second rib 86 is disposed in a second recess of the plurality of recesses 52, and the third rib 88 is disposed in a third recess of the plurality of recesses 52. As the actuator 18 is moved from its first position to its second position, each of the ribs 84, 86, 88 is advanced from its respective recess of the plurality of recesses 52 to another, different, recess of the plurality of recesses 52. For example, the first rib 84 is advanced to a fourth recess of the plurality of recesses 52 that is different than the first recess of the plurality of recesses 52, the second rib 86 is advanced to a fifth recess of the plurality of recesses 52 that is different than the second recess of the plurality of recesses 52, and the third rib 88 is advanced to a sixth recess of the plurality of recesses 52 that is different than the third recess of the plurality of recesses 52. When a protuberance 102 is disposed within a recess of the plurality of recesses 52, a degree of resistance to movement of the actuator 18 relative to the housing 16 is provided, which prevents the selective fluid barrier valve device 10 from moving from its second configuration to its first configuration without the application of force on the actuator 18. The plurality of recesses 52 provides various resting positions for each protuberance 102 and also provides tactile feedback to a user to indicate that the actuator 18 is being advanced around the circumference of the housing 16.

Optionally, the housing body and/or the actuator body can define any suitable structure that prevents the actuator from being moved beyond the second position (e.g., a location in which the sleeve 20 is in a closed configuration) or in a direction that could damage the device (e.g., in a counterclockwise direction when the actuator is in the first position). For example, the housing body can define a first protuberance and a second protuberance and the actuator can define a third protuberance. Each of the first protuberance and the second protuberance is disposed on the third portion of the housing and extends outward from the outer surface of the housing and away from the lengthwise axis of the housing. The third protuberance defined by the actuator extends outward from the inner surface of the actuator and toward the lengthwise axis of the actuator. When the selective fluid barrier valve device is assembled, the third protuberance is disposed between the first protuberance and the second protuberance defined by the housing such that the actuator is prevented from moving beyond where the third protuberance contacts the first protuberance and where the third protuberance contacts the second protuberance.

While a plurality of recesses 52 defined on the housing 16 and a plurality of ribs 84, 86, 88 have been illustrated as providing a mechanism for maintaining the position of the actuator 18 relative to the housing 16 when no outside force is applied to the actuator 18, any suitable structural configuration capable of allowing movement between an actuator and a housing and maintaining the position of the actuator relative to the housing when no outside force is applied to the actuator can be used. Skilled artisans will be able to select a suitable structural configuration to include on a selective fluid barrier valve device to maintain the position of an actuator relative to a housing when no outside force is being applied to the actuator according to a particular embodiment based on various considerations, including the material(s) that forms the actuator and/or the housing. For example, alternative embodiments can include a housing that defines a plurality of ribs such that each rib of the plurality of ribs is sized and configured to be received by a recess of a plurality of recesses defined by an actuator. Alternative to the actuator defining a plurality of ribs, an actuator can define one or more cavities that extend from the inner surface of the actuator and toward the outer surface. Each cavity is sized and configured to receive a biasing device (e.g., spring) and an engagement member. The biasing device is disposed between the end of the cavity and the engagement member. The engagement member is biased toward the housing and is sized and configured to be contained within the cavity such that a portion of the engagement member extends beyond the inner surface of the actuator and contacts the outer surface of the housing (e.g., can interact with the plurality of recesses defined by the housing to maintain the position of the actuator relative to the housing). The engagement member can comprise any suitable component having any suitable structural configuration. For example, the engagement member can comprise a spherical member, a ball, a rounded member, or any other suitable structure that is capable of interacting with the plurality of recesses defined by the housing. The engagement member can be free of attachment to the biasing member, or can be attached to the biasing member using any suitable technique or method, such as those described herein.

Each of the first cavity 90, the second cavity 92, and the third cavity 94 extends into the actuator body 74 from the inner surface 98 toward the outer surface 96 and is sized and configured to receive a portion of a wire member (e.g., first wire member 22, second wire member 24, third wire member 26). In the embodiment illustrated, each of the cavities 90, 92, 94 is defined on the shoulder 80 of the actuator 18 and extends from an opening defined on the shoulder 80 and toward the proximal end 70 of the actuator 18. However, alternative embodiments can define one or more cavities on any other portion of the inner surface of the actuator. The first cavity 90 is disposed a first distance from the second cavity 92, the second cavity 92 is disposed a second distance from the third cavity 94, and the third cavity 94 is disposed a third distance from the first cavity 90. In the illustrated embodiment, the first distance, the second distance, and the third distance are equal to one another and each of the first distance, the second distance, and the third distance is measured along the inner surface 98 of the actuator 18. However, alternative embodiments can include a first cavity that is disposed a first distance from a second cavity, the second cavity is disposed a second distance from a third cavity, and the third cavity is disposed a third distance from the first cavity such that the first distance is different than the second distance and the second distance is the same as, or different than, the third distance. Thus, alternative embodiments can include a plurality of cavities such that a first distance between a first cavity and a second cavity is different than a second distance between the second cavity and a third cavity, or between the second cavity and the first cavity.

The openings of each of the cavities 90, 92, 94 are disposed on a plane that is disposed orthogonal to the lengthwise axis 11 of the selective fluid barrier valve device 10. However, alternative embodiments can include an actuator that defines a plurality of cavities such that at least one, or more than one, cavity is defined on a first plane that is disposed orthogonal to the lengthwise axis of the selective fluid barrier valve device and at lease one, or more than one, cavity is disposed on a second plane that is different than the first plane and is disposed orthogonal to the lengthwise axis of the selective fluid barrier valve device. Each of the cavities 90, 92, 94 has a lengthwise axis 107 that is disposed at an angle relative to the lengthwise axis 11 of the selective fluid barrier valve device 10 (i.e., a plane that contains the lengthwise axis 11 of the selective fluid barrier valve device 10). In the illustrated embodiment, the axis 107 is parallel to the lengthwise axis 11 of the selective fluid barrier valve device 10. However, alternative embodiments can include a cavity that is disposed at any suitable angle relative to the lengthwise axis of a selective fluid barrier valve device (i.e., a plane that contains the lengthwise axis of a selective fluid barrier valve device), such as angles that are equal to, substantially equal to, or about 0 degrees, angles that are oblique, angles that are obtuse, angles that are acute, and any other angle considered suitable for a particular embodiment. Any angle that is capable of securing an end of a wire member and does not impart kinking or excessive stress on the wire member is considered suitable While the actuator 18 has been illustrated as having a particular structural arrangement, an actuator can have any suitable structural arrangement and skilled artisans will be able to select a suitable structural arrangement for an actuator according to a particular embodiment based on various considerations, including the number of wire members included in a selective fluid barrier valve device. For example, while a protuberance has been illustrated, an actuator body can define any suitable structure capable of providing a mechanism to moveably attach an actuator to a housing, such as a groove that is sized and configured to receive a protuberance defined by the housing. While the actuator body 74 has been illustrated as defining a plurality of ribs 84, 86, 88 and a plurality of cavities 90, 92, 94, an actuator body can define any suitable number of ribs and/or cavities, such as one, at least one, two, a plurality, three, four, five, six, and any other number considered suitable for a particular embodiment.

In the illustrated embodiment, and as shown in FIG. 2, the sleeve 20 has a proximal end 110, a distal end 112, a lengthwise axis 113, and a sleeve body 114 that defines a passageway 116, a shaft 118, a flange 120, an outer surface 121, and an inner surface 122. The distal end 112 of the sleeve 20 is disposed between the housing 16 and the connector 28 and the proximal end 112 of the sleeve 20 is disposed within the passageway 46 defined by the housing 16. The flange 120 of the sleeve 20 contacts the distal end 32 of the housing 16 and, when the connector 28 is attached to the housing 16, the distal end 112 of the sleeve 20 is fixed relative to the housing 16. The sleeve 20 is moveable between a first configuration and a second configuration, as described in more detail herein.

Figure 8A:
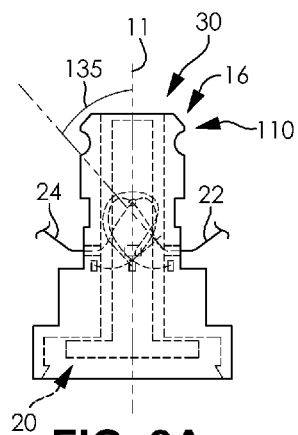
FIG. 8A is a side view of the selective fluid barrier valve device illustrated in FIG. 1. The selective fluid barrier valve device is illustrated in a first configuration. Each of the actuator and connector has been omitted for clarity.
Figure 8B:
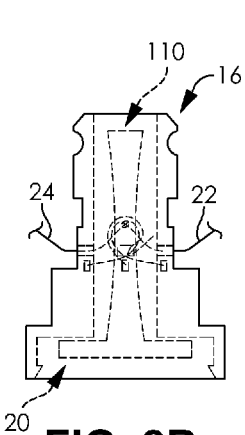
FIG. 8B is another side view of the selective fluid barrier valve device illustrated in FIG. 1. The selective fluid barrier valve device is illustrated between a first configuration and a second configuration. Each of the actuator and connector has been omitted for clarity.
Figure 8C:
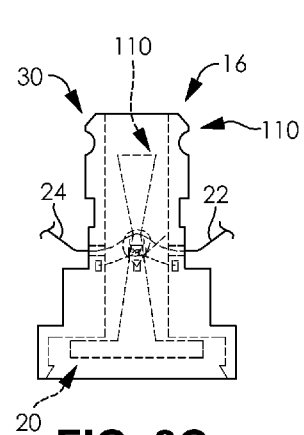
FIG. 8C is another side view of the selective fluid barrier valve device illustrated in FIG. 1. The selective fluid barrier valve device is illustrated in a second configuration. Each of the actuator and connector has been omitted for clarity.
Figure 10A:
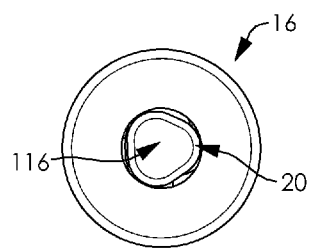
FIG. 10A is another end view of the distal end of the selective fluid barrier valve device illustrated in FIG. 1. The selective fluid barrier valve device is illustrated in a first configuration. Each of the actuator and the connector has been omitted for clarity.
Figure 10B:
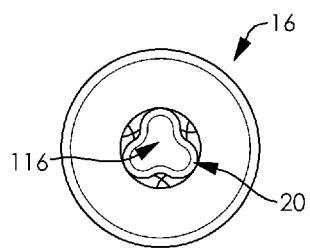
FIG. 10B is another end view of the distal end of the selective fluid barrier valve device illustrated in FIG. 1. The selective fluid barrier valve device is illustrated between a first configuration and a second configuration. Each of the actuator and the connector has been omitted for clarity.
Figure 10C:
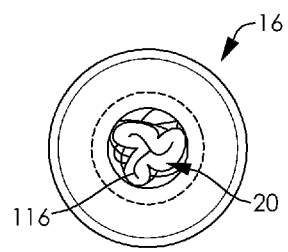
FIG. 10C is another end view of the distal end of the selective fluid barrier valve device illustrated in FIG. 1. The selective fluid barrier valve device is illustrated in a second configuration. Each of the actuator and the connector has been omitted for clarity.
Figure 11:
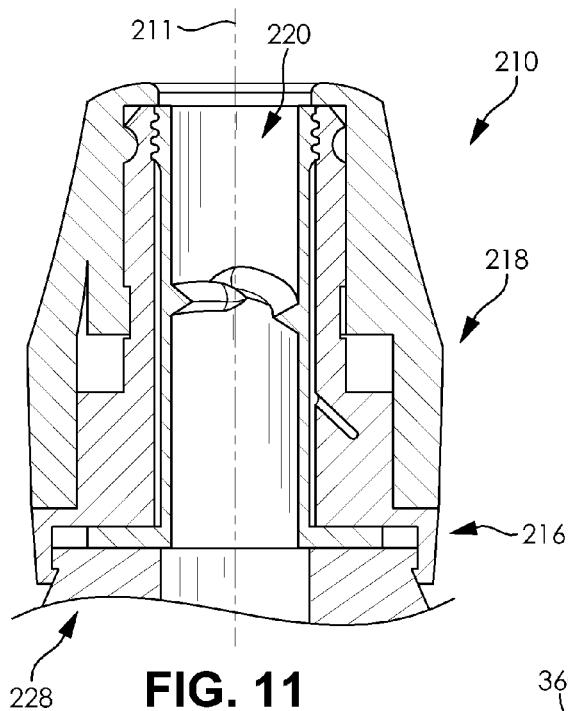
FIG. 11 is a partial sectional view of another example selective fluid barrier valve device taken along the lengthwise axis of the selective fluid barrier valve device. The selective fluid barrier valve device is illustrated in a first configuration.
Figure 12:
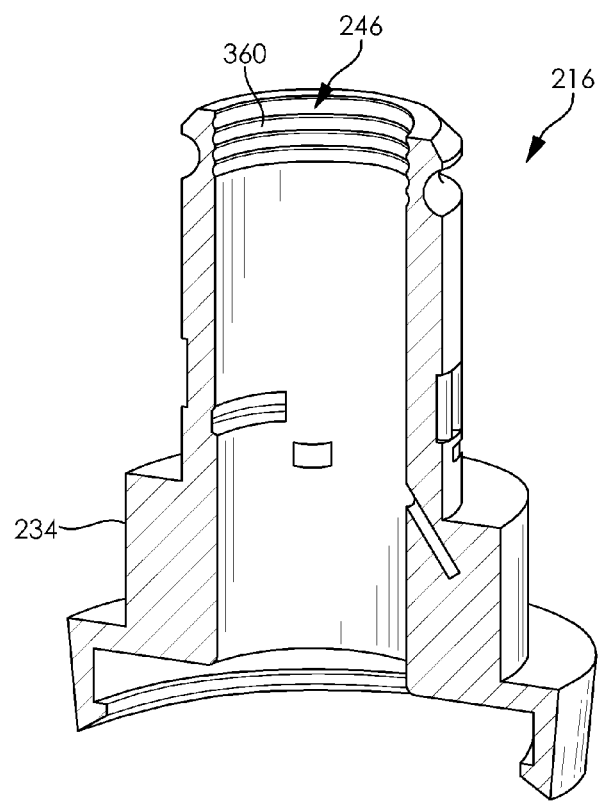
FIG. 12 is a perspective sectional view of the housing of the selective fluid barrier valve device illustrated in FIG. 11 taken along the lengthwise axis of the housing.
Figure 13:
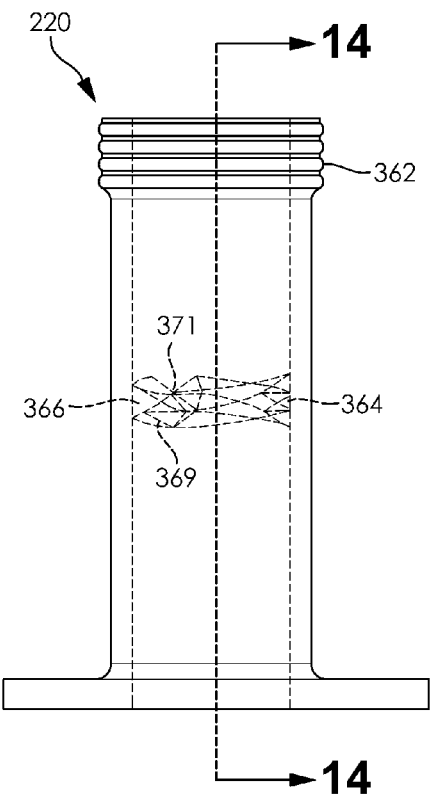
FIG. 13 is a side view of the sleeve of the selective fluid barrier valve device illustrated in FIG. 11.
Figure 14:
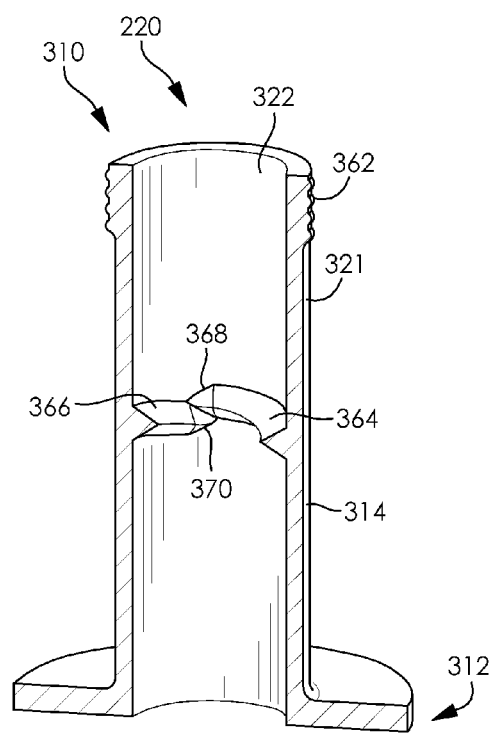
FIG. 14 is a perspective cross-sectional view of the sleeve illustrated in FIG. 13, taken along line 14-14.

The passageway 116 extends through the sleeve 20 from the proximal end 110 to the distal end 112 of the sleeve 20 and is sized and configured to receive a medical device. The passageway 116 is moveable between a first configuration, as illustrated in FIGS. 8A and 10A, and a second configuration, as illustrated in FIGS. 8C and 10C. In the first configuration, the passageway 116 defined by the sleeve 20 is open such that fluid can pass through the passageway. In the second configuration, the passageway 116 defined by the sleeve 20 is closed such that fluid is prevented from passing through the passageway 116.

The shaft 118 extends from the proximal end 110 to the distal end 112 of the sleeve 20 and is sized and configured to be received by the passageway 46 defined by the housing 16. The flange 120 extends from the shaft 118 and away from the lengthwise axis 113 of the sleeve 20. The flange 120 provides a mechanism for releasably attaching the sleeve 20 between the housing 16 and the connector 28 and for preventing proximal advancement of the sleeve 20 beyond where the flange 120 contacts the third shoulder 48 defined by the housing body 34. Optionally, the sleeve body can define one or more recesses and/or ridges on the outer surface of the sleeve to aid in moving the sleeve from the first configuration to the second configuration. For example, each recess can be sized and configured to receive a portion of a wire member. This optional structural configuration provides a mechanism for positioning each wire member at a particular location on the outer surface of the sleeve (e.g., within a recess).

The sleeve 20 can be formed of any suitable material and using any suitable manufacturing technique, and skilled artisans will be able to select a suitable material and technique to form a sleeve according to a particular embodiment based on various considerations, including the material(s) that forms the housing of an embodiment. Example materials considered suitable to form a sleeve include biocompatible materials, materials that can be made biocompatible, compliant materials, elastomeric materials, polymers, polyurethanes, polyisoprene, polyethylene, polyvinyl chloride, polystyrene, silicone, silicone blends, and any other material considered suitable for a particular embodiment. Example techniques considered suitable to form a sleeve include injection molding, casting, extrusion, and any other technique considered suitable for a particular embodiment.

The first wire member 22 has a first end 124 and a second end 126. The first end 124 of the first wire member 22 is attached to the housing 16 and is disposed within the first cavity 62 defined by the housing 16. The second end 126 of the first wire member 22 is attached to the actuator 18 and is disposed within the first cavity 90 defined by the actuator 18. The first wire member 22 extends from the first end 124 disposed within the first cavity 62 defined by the housing 16, around a portion of the outer surface 121 of the sleeve 20 between the housing 16 and the sleeve 20, through the first opening 56 defined by the housing 16, and to the second end 126 disposed within the first cavity 90 defined by the actuator 18. When the first wire member 22 is in the first configuration, the portion of the first wire member 22 that extends around the outer surface 121 of the sleeve 20 is disposed at an oblique angle relative to the lengthwise axis 11 of the selective fluid barrier valve device 10 (i.e., a plane that contains the lengthwise axis 11 of the selective fluid barrier valve device 10).

The first end 124 of the first wire member 22 is disposed a first distance from the proximal end 30 of the housing 16 and the second end 126 of the first wire member 24 is disposed a second distance from the proximal end 30 of the housing 16. A portion of the first wire member 22 disposed between the first end 124 and the second end 126 (i.e., the portion that extends around the sleeve 20) is disposed a third distance from the proximal end 30 of the housing 16. In the illustrated embodiment, the third distance is less than the first distance and the second distance. However, alternative embodiments can include a wire member that has a portion disposed between the first end and the second end of the wire member that is disposed a distance from the proximal end of the housing that is equal to, substantially equal to, or greater than the distance the first end and/or the second end of the wire member is disposed from the proximal end of the housing.

The second wire member 24 has first end 128 and a second end 130. The first end 128 of the second wire member 24 is attached to the housing 16 and is disposed within the second cavity 64 defined by the housing 16. The second end 130 of the second wire member 24 is attached to the actuator 18 and is disposed within the second cavity 92 defined by the actuator 18. The second wire member 24 extends from the first end 128 disposed within the second cavity 64 defined by the housing 16, around a portion of the outer surface 121 of the sleeve 20 between the housing 16 and the sleeve 20, through the second opening 58 defined by the housing 16, and to the second end 130 disposed within the second cavity 92 defined by the actuator 18. When the second wire member 24 is in the first configuration, the portion of the second wire member 24 that extends around the outer surface 121 of the sleeve 20 is disposed at an oblique angle relative to the lengthwise axis 11 of the selective fluid barrier valve device 10 (i.e., a plane that contains the lengthwise axis 11 of the selective fluid barrier valve device 10).

The first end 128 of the second wire member 24 is disposed a first distance from the proximal end 30 of the housing 16 and the second end 130 of the second wire member 24 is disposed a second distance from the proximal end 30 of the housing 16. A portion of the second wire member 24 disposed between the first end 128 and the second end 130 (e.g., the portion that extends around the sleeve 20) is disposed a third distance from the proximal end 30 of the housing 16. In the illustrated embodiment, the third distance is less than the first distance and the second distance. However, alternative embodiments can include a second wire member that has a portion disposed between the first end and the second end of the wire member that is disposed a distance from the proximal end of the housing that is equal to, substantially equal to, or greater than the distance the first end and/or the second end of the wire member is disposed from the proximal end of the housing.

The third wire member 26 has a first end 132 and a second end 134. The first end 132 of the third wire member 26 is attached to the housing 16 and is disposed within the third cavity 66 defined by the housing 16. The second end 134 of the third wire member 26 is attached to the actuator 18 and is disposed within the third cavity 94 defined by the actuator 18. The third wire member 26 extends from the first end 132 disposed within the third cavity 66 defined by the housing 16, around a portion of the outer surface 121 of the sleeve 20 between the housing 16 and the sleeve 20, through the third opening 60 defined by the housing 16, and to the second end 134 disposed within the third cavity 94 defined by the actuator 18. When the third wire member 26 is in the first configuration, the portion of the third wire member 26 that extends around the outer surface 121 of the sleeve 20 is disposed at an oblique angle relative to the lengthwise axis 11 of the selective fluid barrier valve device 10 (i.e., a plane that contains the lengthwise axis 11 of the selective fluid barrier valve device 10). Alternatively, one or more of the wire members included in a selective fluid barrier valve device can be passed through a portion of the sleeve body. For example, alternative embodiments can include a sleeve that defines one or more protuberances that extend from the outer surface of the sleeve and along a portion of the circumference of the outer surface of the sleeve. Each protuberance defines a passageway sized and configured to receive a portion of a wire member such that the wire member can be passed through the passageway defined by a protuberance.

The first end 132 of the third wire member 26 is disposed a first distance from the proximal end 30 of the housing 16 and the second end 134 of the third wire member 26 is disposed a second distance from the proximal end 30 of the housing 16. A portion of the third wire member 26 disposed between the first end 132 and the second end 134 (e.g., the portion that extends around the sleeve 20) is disposed a third distance from the proximal end 30 of the housing 16. In the illustrated embodiment, the third distance is less than the first distance and the second distance. However, alternative embodiments can include a third wire member that has a portion disposed between the first end and the second end of the wire member that is disposed a distance from the proximal end of the housing that is equal to, substantially equal to, or greater than the distance the first end and/or the second end of the wire member is disposed from the proximal end of the housing.

Attachment between a wire member and a housing and/or an actuator can be accomplished using any suitable method or technique, and skilled artisans will be able to select a suitable method or technique to attach a wire member to a housing and/or an actuator according to a particular embodiment based on various considerations, including the material(s) that forms the wire member. Example methods and techniques considered suitable to attach a wire member to a housing and/or an actuator include using adhesives, welding, fusing, providing a friction fit between the wire member and the housing and/or actuator, and any other method or technique considered suitable for a particular embodiment. For example, a wire member can have an outside diameter that is greater than the inside diameter of a cavity defined by a housing and/or actuator such that a friction fit between the wire member and the housing and/or actuator can be achieved.

In the illustrated embodiment, and as shown in FIG. 8A, when the selective fluid barrier valve device 10 is in the first configuration each of the wire members 22, 24, 26 is disposed at an oblique angle 135 relative to the lengthwise axis 11 of the selective fluid barrier valve device 10 (i.e., a plane that contains the lengthwise axis 11 of the selective fluid barrier valve device 10) that is equal to 35 degrees. However, other angles are considered suitable, and skilled artisans will be able to select a suitable angle to position a wire member relative to a lengthwise axis of a selective fluid barrier valve device (i.e., a plane that contains the lengthwise axis 11 of the selective fluid barrier valve device 10) according to a particular embodiment based on various considerations, including the material(s) that forms the sleeve of an embodiment. Example angles considered suitable to position a wire member relative to the lengthwise axis of a selective fluid barrier valve device (i.e., a plane that contains the lengthwise axis 11 of the selective fluid barrier valve device 10) include angles equal to, substantially equal to, or about 35 degrees, 90 degrees, angles between about 0 degrees and about 180 degrees, angles between 0 degrees and 180 degrees, and any other angle considered suitable for a particular embodiment. For example, an alternative embodiment can include a sleeve that defines a flange on the proximal end of the sleeve that is in contact with the proximal end of the housing. The sleeve can include a distal end that is free to move along the lengthwise axis of the selective fluid barrier valve device. In this alternative embodiment, example angles considered suitable to position a wire member relative to the lengthwise axis of the selective fluid barrier valve device (i.e., a plane that contains the lengthwise axis 11 of the selective fluid barrier valve device 10) include angles that are equal to, substantially equal to, or about 90 degrees, or greater than 90 degrees.

Figure 9A:
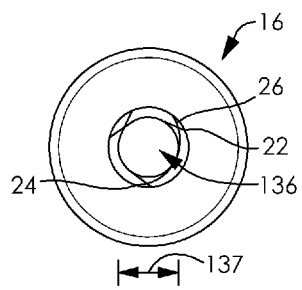
FIG. 9A is an end view of the distal end of the selective fluid barrier valve device illustrated in FIG. 1. The selective fluid barrier valve device is illustrated in a first configuration. Each of the actuator, the connector, and the sleeve has been omitted for clarity.
Figure 9B:
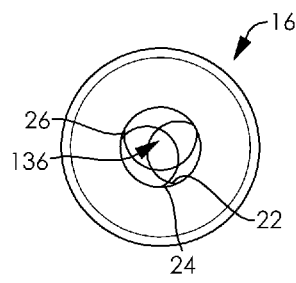
FIG. 9B is another end view of the distal end of the selective fluid barrier valve device illustrated in FIG. 1. The selective fluid barrier valve device is illustrated between a first configuration and a second configuration. Each of the actuator, the connector, and the sleeve has been omitted for clarity.
Figure 9C:
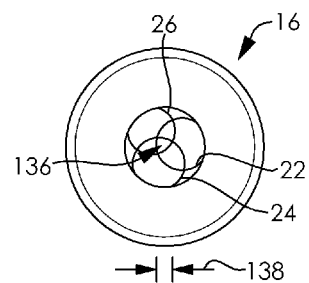
FIG. 9C is another end view of the distal end of the selective fluid barrier valve device illustrated in FIG. 1. The selective fluid barrier valve device is illustrated in a second configuration. Each of the actuator, the connector, and the sleeve has been omitted for clarity.

In the illustrated embodiment, each of the wire members 22, 24, 26 is moveable between a first configuration and a second configuration and is configured such that an opening 136 is defined within the housing 16 between the wire members 22, 24, 26. In the first configuration, as shown in FIGS. 8A, 9A, and 10A, each of the wire members 22, 24, 26 is in a relaxed configuration and has a portion disposed between its first end and its second end that is disposed a first distance from the lengthwise axis 11 of the selective fluid barrier valve device 10. In the first configuration, the opening 136 has a first diameter 137. In the second configuration, as shown in FIGS. 8C, 9C, and 10C, each of the wire members 22, 24, 26 is in a tensioned configuration such that the portion of each of the wire members 22, 24, 26 that is disposed between its first end and its second end is disposed a second distance from the lengthwise axis 11 of the selective fluid barrier valve device 10. The second distance is less than the first distance. In the second configuration, the opening 136 has a second diameter 138 that is less than the first diameter 137.

Each of the wire members 22, 24, 26 can be formed of any suitable material and using any suitable manufacturing technique, and skilled artisans will be able to select a suitable material and technique to form a wire member according to a particular embodiment based on various considerations, including the material(s) that forms the sleeve of an embodiment. Example materials considered suitable to form a wire member include biocompatible materials, materials that can be made biocompatible, braided materials, wound materials, twisted materials, noncompliant materials, metals such as steel, stainless steel, titanium, nickel-titanium alloys, polymers, polypropylene, polyester, Nylon, polyethylene, polyvinyl chloride, polystyrene, compliant materials, flexible materials (e.g., materials that are relatively more flexible than the material that forms the housing), and any other material considered suitable for a particular embodiment. Example techniques considered suitable to form a wire member include injection molding, casting, extrusion, and any other technique considered suitable for a particular embodiment.

A wire member, such as the first wire member 22, the second wire member 24, and the third wire member 26, can have any suitable structure and comprise any suitable number of strands and/or fibers that are twisted, or otherwise interconnected to one another. For example, a wire member can have a cross-sectional configuration that is round, substantially round, rectangular, square, oval, and any other configuration considered suitable for a particular embodiment and can include any suitable number of strands and/or fibers, such as one, at least one, two, a plurality, three, four, and any other number considered suitable for a particular embodiment. For example, a wire member can comprise a suture or a cable.

While the selective fluid barrier valve device 10 has been illustrated as including a first wire member 22, a second wire member 24, and a third wire member 26, a selective fluid barrier valve device can include any suitable number of wire members. Skilled artisans will be able to select a suitable number of wire members to include in a selective fluid barrier valve device according to a particular embodiment based on various considerations, including the material(s) that forms the sleeve of an embodiment. Example number of wire members considered suitable to include in a selective fluid barrier valve device include one, at least one, two, a plurality, three, four, five, and any other number considered suitable for a particular embodiment.

Figure 7:
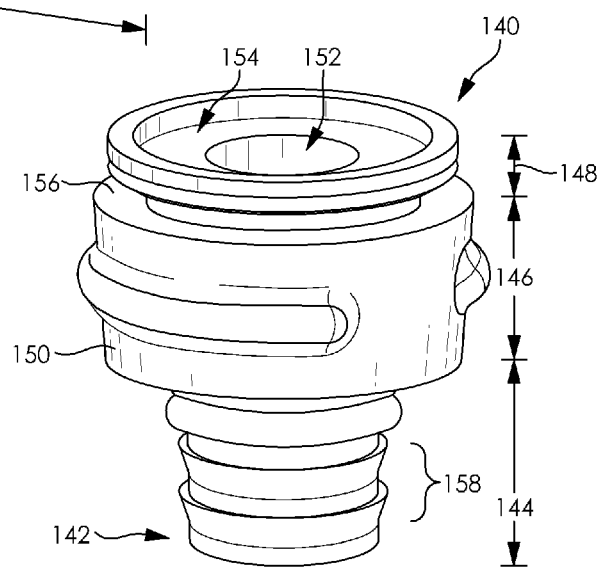
FIG. 7 is a perspective view of the connector of the selective fluid barrier valve device illustrated in FIG. 1.

In the illustrated embodiment, and as shown in FIG. 7, the connector 28 has a proximal end 140, a distal end 142, a first portion 144, a second portion 146, a third portion 148, and a connector body 150 that defines a passageway 152, a recess 154, a groove 156, and a plurality of barbs 158. Optionally, the connector 28 can be omitted from the selective fluid barrier valve device 10 and can be provided as a separate component.

The first portion 144 of the connector 28 extends from the distal end 142 toward the proximal end 140 of the connector 28. The second portion 146 of the connector 28 extends from the first portion 144 and toward the proximal end 140 of the connector 28. The third portion 148 of the connector 28 extends from the second portion 146 to the proximal end 140 of the connector 28. Thus, the second portion 146 is disposed between the first portion 144 and the third portion 148.

The passageway 152 extends through the connector 28 from the proximal end 140 to the distal end 142 of the connector 28 and is sized and configured to receive a medical device. When the selective fluid barrier valve device 10 is assembled, as illustrated in FIG. 1, the passageway 116 defined by the sleeve 20 is in communication with the passageway 152 defined by the connector 28.

The recess 154 extends into the third portion 148 of the connector 28 from the proximal end 140 and extends toward the distal end 142. The recess 154 is sized and configured to receive a portion of the sleeve 20 (e.g., flange 120). The groove 156 extends into the connector body 150 toward the lengthwise axis 11 of the selective fluid barrier valve device 10 and is disposed on the third portion 148 of the connector 28. In the embodiment illustrated, the groove 156 extends around the entire circumference of the outer surface of the connector 28. However, alternative embodiments can include a connector that defines a groove that extends around a portion of the outer surface of the connector. The groove 156 is sized and configured to receive a portion of the protuberance 54 defined by the housing 16 such that the connector 28 can be releasably attached to the housing 16 (e.g., a snap fit configuration is achieved between the housing 16 and the connector 28). Optionally, the connector of an embodiment can be fixedly attached to the housing using any suitable technique or method, such as those described herein, such that it is not moveable relative to the housing.

The plurality of barbs 158 is defined on the first portion 144 of the connector 28. Each barb of the plurality of barbs 158 extends from the outer surface of the connector 28 and away from the lengthwise axis 11 of the selective fluid barrier valve device 10. The plurality of barbs 158 provides a mechanism for releasably attaching another component (e.g., medical device, tubular member) to the connector 28.

Each of the housing 16, the actuator 18, and the connector 28 can be formed of any suitable material and using any suitable manufacturing technique, and skilled artisans will be able to select a suitable material and technique to form a housing, an actuator, and a connector according to a particular embodiment based on various considerations, including the material(s) that forms the sleeve of an embodiment. Example materials considered suitable to form a housing, an actuator, and/or a connector include biocompatible materials, materials that can be made biocompatible, metals such as stainless steel, titanium, nickel-titanium alloys, polymers, polyethylene, polyvinyl chloride, polystyrene, polycarbonate, polyacetal, polypropylene, terpolymers, acrylonitrile butadiene styrene (ABS), and any other material considered suitable for a particular embodiment. Example techniques considered suitable to form a housing, an actuator, and/or a connector include injection molding, casting, and any other technique considered suitable for a particular embodiment.

While a snap fit attachment has been illustrated between the housing 16 and the actuator 18 and between the housing 16 and the connector 28, any suitable form of attachment can be used between these components. Skilled artisans will be able to select a suitable form of attachment between a housing and an actuator and between a housing and a connector according to a particular embodiment based on various considerations, such as the materials that form the components. For example, an actuator can be positioned on a housing and a pin can be positioned in a cavity defined by the housing between the proximal end of the actuator and the proximal end of the housing to prevent the actuator from becoming free of the housing. Alternatively, or in combination with using a pin, a morse taper and/or threaded attachment can be used between a housing and a connector.

As illustrated in FIGS. 8A, 9A, and 10A, when the actuator 18 is in the first position, the selective fluid barrier valve device 10 is in the first configuration, the passageway 116 defined by the sleeve 20 is open and fluid can pass through the passageway 116, and each of the wire members 22, 24, 26 is in its first configuration. When the actuator 18 is in the first position, the proximal end 110 of the sleeve 20 is disposed a first distance from the proximal end 30 of the housing 16, as shown in FIG. 8A.

Movement of the actuator 18 from the first position to the second position can be accomplished in any suitable manner and using any suitable process and/or technique, such as by maintaining the position of the housing 16 and applying a rotational force to the actuator 18 in a clockwise direction, as illustrated by arrow 159 in FIG. 1, such that each protuberance 102 of the ribs 84, 86, 88 of the actuator 18 moves from a recess of the plurality of recesses 76 to another recess of the plurality of recesses 76. FIGS. 8B, 9B, and 10B illustrate the configuration of the housing 16, the sleeve 20, and the wire members 22, 24, 26 when the actuator 18 is between the first position and the second position. In this configuration, each of the selective fluid barrier valve device 10, the sleeve 20, the first wire member 22, the second wire member 24, and the third wire member 26 is between the first configuration and the second configuration. The rotational force is applied to the actuator 18 until the actuator 18 is moved to its second position, and the sleeve 20 is moved to its second configuration such that the passageway 116 defined by the sleeve 20 is closed and fluid is prevented from passing through the passageway 116. When the sleeve 20 is in the second configuration, the material that forms the sleeve 20 contacts itself to close the passageway 116 defined by the sleeve 20. However, when one or more medical devices are passed though the passageway 116 defined by the sleeve 20, the material that forms the sleeve 20 contacts a portion of one or more of the medical devices to close the passageway 116 such that fluid is prevented from passing through the passageway 116.

FIGS. 8C, 9C, and 10C illustrate the configuration of the housing 16, the sleeve 20, and the wire members 22, 24, 26 when the actuator 18 in the second position. In this configuration, each of the selective fluid barrier valve device 10, the sleeve 20, the first wire member 22, the second wire member 24, and the third wire member 26 is in the second configuration. As shown in FIG. 8C, when the actuator 18 is in the second position, the proximal end 110 of the sleeve 20 is disposed a second distance from the proximal end 30 of the housing 16. In the illustrated embodiment, the second distance is greater than the first distance such that the proximal end 110 of the sleeve 20 is advanced toward the distal end 32 of the housing 16 as the actuator 18 is moved from its first position to its second position. Thus, the proximal end 110 of the sleeve 20 is moveable relative to the housing 16. However, alternative embodiments can include a sleeve that has a proximal end that is fixed relative to the housing.

Movement of the actuator 18 from its second configuration to its first configuration can be accomplished in any suitable manner and using any suitable process and/or technique, such as by maintaining the position of the housing 16 and applying a rotational force to the actuator 18 in a counterclockwise direction, opposite the directed illustrated by arrow 159, such that each protuberance 102 of the ribs 84, 86, 88 of the actuator 18 moves from a recess of the plurality of recesses 76 to another recess of the plurality of recesses 76. Movement of the actuator 18 from its second position to its first position moves the sleeve 20 from its second configuration in which the passageway 116 defined by the sleeve 20 is closed to fluid flow to the first configuration in which the passageway 116 defined by the sleeve 20 is open to fluid flow. Movement of the actuator 18 from its second position to its first position advances the proximal end 110 of the sleeve 20 toward the proximal end 30 of the housing 16. In embodiments in which a connector is fixedly attached to a housing such that it is not moveable relative to the housing, the position of the housing and/or the connector can be maintained to accomplish movement of the actuator between its first position and its second position.

The selective fluid barrier valve device 10 is configured such that any suitable medical device can be passed through the passageway 116 defined by the sleeve 20 that has an outside diameter that is less than the inside diameter of the passageway 116 defined by the sleeve 20 when it is in the first configuration. Thus, the sleeve 20 of the selective fluid barrier valve device 10 can be sized and configured such that one or more medical devices can be passed through the passageway 116 defined by the sleeve 20. The selective fluid barrier device 10 can be selectively moved between its first configuration and its second configuration based on the treatment being performed.

Optionally, a fluid barrier valve device can include one or more sealing members disposed distal to the sleeve. For example, a sealing member can be attached to the housing within the housing passageway and/or to the connector within the connector passageway. A sealing member can be formed of a soft, semi-rigid, or elastic material that is able to provide sufficient flexibility and resilience to the device inserted through the sealing member, to stretch to the extent required to allow the device to traverse the sealing member, and to enable the opening created by the device to substantially return to a pre-stretched condition when the device is removed. For example, the sealing member can comprise a disc that has a predefined slit, or that omits the inclusion of a predefined slit. A sealing member can be formed of any suitable material, such as elastomers, ePFTE, nylon, polyethylene, silicone, urethane, other polymeric materials, the materials described herein, and any other material considered suitable for a particular embodiment. A sealing member can have any suitable configuration, including round, square, or any other configuration that is substantially similar to, or compatible with, the passageway defined by a housing and/or connector. A sealing member can have any suitable thickness, length, width, or diameter, depending on the structural arrangement of the selective fluid barrier valve device (e.g., housing, connector), and the structural arrangement of the devices that are intended to traverse the sealing member.

Optionally, a selective fluid barrier valve device can be biased to the second configuration such that the actuator is biased to the second position. This can be accomplished using any suitable structural configuration or component. For example, a torsion spring can be positioned between the housing and the actuator and can be attached to the housing and the actuator such that when no outside forces are applied to the selective fluid barrier valve device, the spring positions the actuator in the second position.

Alternative embodiments can include a sleeve that has a proximal end that is disposed proximal to the proximal end of the housing a first distance. In these alternative embodiments, as the actuator is moved from its first position to its second position, the proximal end of the sleeve advances toward the proximal end of the housing such that it is disposed a second distance from the distal end of the housing. The second distance can be less than, or greater than, the first distance. Alternative embodiments can be configured such that movement of the actuator in a counterclockwise direction moves the actuator from its first position to its second position and each of the sleeve and the wire members are moved from their respective first configurations to their second configurations and movement of the actuator in a clockwise direction moves the actuator from its second position to its first position and each of the sleeve and the wire members are moved from their respective second configurations to their first configurations.

An alternative to including a sleeve, such as the sleeve 20 described with respect to FIGS. 1, 2, 3, 4, 5, 6, 7, 8A, 8B, 8C, 9A, 9B, 9C, 10A, 10B, and 10C, a selective fluid barrier valve device can include a sleeve that has a proximal portion that is folded over on itself when the sleeve is in the first configuration. In these alternative embodiments, a portion, or the entirety, of the proximal end of the sleeve is attached to the housing (e.g., inner surface of the housing, outer surface of the housing, at the proximal end of the housing) and the proximal end of the sleeve is disposed distal to the portion of the sleeve when the sleeve is in the first configuration. The proximal end of the sleeve can be attached to the housing using any suitable method or technique, such as using adhesives, welding, fusing, and any other method or technique considered suitable for a particular embodiment. In these alternative embodiments, as the sleeve is moved from the first configuration to the second configuration, the portion of the sleeve disposed proximal to the proximal end of the sleeve advances toward the distal end of the housing. In the second configuration, the configuration of the portion of the sleeve will change based on the amount of the sleeve that is folded over on itself. For example, when the sleeve is in the second configuration, the portion of the sleeve can be disposed proximal to, or distal to, the proximal end of the sleeve. As the sleeve is moved from the second configuration to the first configuration, the portion of the sleeve advances away from the distal end of the housing. The inclusion of a sleeve that is attached to the housing prevents a device or fluid from being introduced between the sleeve and the housing during use.

FIGS. 11, 12, 13, and 14 illustrate another selective fluid barrier valve device 210. Selective fluid barrier valve device 210 is similar to the selective fluid barrier valve device 10 illustrated in FIGS. 1, 2, 3, 4, 5, 6, 7, 8A, 8B, 8C, 9A, 9B, 9C, 10A, 10B, and 10C and described above, except as detailed below. With respect to selective fluid barrier valve device 210, reference numbers in FIGS. 11, 12, 13, and 14 refer to the same structural element or feature referenced by the same number in FIGS. 1, 2, 3, 4, 5, 6, 7, 8A, 8B, 8C, 9A, 9B, 9C, 10A, 10B, and 10C, offset by 200. Thus, selective fluid barrier valve device 210 comprises a housing 216, an actuator 218, a sleeve 220, and a connector 228. The first wire member (e.g., first wire member 22), second wire member (e.g., second wire member 24), and third wire member (e.g., third wire member 26) have been omitted from FIGS. 11, 12, 13, and 14 for clarity.

In the illustrated embodiment, the housing body 234 defines a plurality of grooves 360 within the passageway 246 defined by the housing 216. Each groove of the plurality of grooves 360 extends into the housing body 234 and away from the lengthwise axis 211 of the selective fluid barrier valve device 210 and is sized and configured to receive a protuberance of the plurality of protuberances 362 defined by the sleeve 220, as described below.

In the illustrated embodiment, the sleeve body 314 defines a plurality of protuberances 362, a first protrusion 364, and a second protrusion 366. The plurality of protuberances 362 extends outward from the outer surface 321 of the sleeve 220 and away from the lengthwise axis 211 of the selective fluid barrier valve device 210. Each protuberance of the plurality of protuberances 362 is sized and configured to be received by a groove of the plurality of grooves 360 defined by the housing 216. In the embodiment illustrated, each protuberance of the plurality of protuberances 362 is disposed in a groove of the plurality of grooves 360 defined by the housing 216. This configuration provides a mechanism for providing additional support to the sleeve 220 during use.

Each of the first protrusion 364 and second protrusion 366 has a tapered configuration and extends from the inner surface 322 of the sleeve 220 and toward the lengthwise axis 211 of the selective fluid barrier valve device 210. The first protrusion 364 has a first end 368 and a second end 369. The second protrusion 366 has a first end 370 and a second end 371. The first end 368 of the first protrusion 364 is disposed between the first end 370 of the second protrusion 366 and the proximal end 310 of the sleeve 220. The second end 369 of the first protrusion 364 is disposed between the second end 371 of the second protrusion 366 and the distal end 312 of the sleeve 220. The first end 370 of the second protrusion 366 is disposed between the first end 368 of the first protrusion 364 and the distal end 312 of the sleeve 220. The second end 371 of the second protrusion 366 is disposed between the second end 369 of the first protrusion 364 and the proximal end 310 of the sleeve 220. Each of the protrusions 364, 366 provides structure within the passageway 316 of the sleeve 220 that prevents fluid from passing through the passageway 316 when the selective fluid barrier valve device 210 is in the second configuration.

While the sleeve body 314 has been illustrated as defining a first protrusion 364 and a second protrusion 366 and each protrusion has been illustrated as having a tapered configuration, a sleeve can define any suitable number of protrusions having any suitable structural configuration. Skilled artisans will be able to select a suitable number of protrusions to define within the passageway of a sleeve and a suitable structural configuration for each protrusion according to a particular embodiment based on various considerations, including the medical device intended to be passed through the passageway defined by the sleeve. Example number of protrusions considered suitable to include within the passageway of a sleeve include one, at least one, two, a plurality, three, four, and any other number considered suitable for a particular embodiment. Example structural arrangements considered suitable for a protrusion include protrusions that have a cross-sectional configuration that is curved, tapered, rectangular, square, semi-circular, and any other configuration considered suitable for a particular embodiment.

While the housing body 234 has been illustrated as defining a plurality of grooves 360 and the sleeve body 314 has been illustrated as defining a plurality of protuberances 362, a housing can define any suitable number of grooves and a sleeve can define any suitable number of protuberances. Example number of grooves and/or protuberances considered suitable to include on a selective fluid barrier valve device include one, at least one, two, a plurality, three, four, and any other number considered suitable for a particular embodiment. Alternative to the housing defining a plurality of grooves and the sleeve defining a plurality of protuberances, a housing body can define a protuberance, or a plurality of protuberances, and a sleeve body can define a groove, or a plurality of grooves.

FIGS. 15, 16, and 17 illustrate another selective fluid barrier valve device 410. Selective fluid barrier valve device 410 is similar to the selective fluid barrier valve device 10 illustrated in FIGS. 1, 2, 3, 4, 5, 6, 7, 8A, 8B, 8C, 9A, 9B, 9C, 10A, 10B, and 10C and described above, except as detailed below. With respect to selective fluid barrier valve device 410, reference numbers in FIGS. 15, 16, and 17 refer to the same structural element or feature referenced by the same number in FIGS. 1, 2, 3, 4, 5, 6, 7, 8A, 8B, 8C, 9A, 9B, 9C, 10A, 10B, and 10C, offset by 400. Thus, selective fluid barrier valve device 410 comprises a housing 416, an actuator 418, a sleeve 420, and a connector 428.

In the illustrated embodiment, the selective fluid barrier valve device 410 omits the inclusion of a second wire member (e.g., second wire member 24) and a third wire member (e.g., third wire member 26). The housing 416 omits the inclusion of a third opening (e.g., third opening 60), a first cavity (e.g., first cavity 62), a second cavity (e.g., second cavity 64), and a third cavity (e.g., third cavity 66). The actuator 418 omits the inclusion of a second cavity (e.g., second cavity 92) and a third cavity (e.g., third cavity 94).

In the illustrated embodiment, the housing body 434 defines the first opening 456 adjacent to the second opening 458 and each of the first opening 456 and the second opening 458 are circular. However, a first opening and second opening can have any suitable structural arrangement, such as oval, rectangular, square, and can be positioned at any suitable location on a housing.

The first wire member 422 has a first end 524 attached to the actuator 418 within the first cavity 490 and a second end 526 attached to the first wire member 422 between the first end 524 and the second end 526. The first wire member 422 extends from the first end 524 disposed within the first cavity 490 defined by the actuator 418, through the first opening 456 defined by the housing 416, around the outer surface 521 of the sleeve 420, through the second opening 458 defined by the housing 416, around the outer surface of the first wire member 422 and is attached to itself between the first end 524 and the second end 526. Thus, the first wire member 422 defines a loop 574 at its second end 526 through which the first wire member 422 is disposed.

In the illustrated embodiment, the first wire member 422 is disposed orthogonally relative to the lengthwise axis 411 of the selective fluid barrier valve device 410 (i.e., a plane that contains the lengthwise axis 411 of the selective fluid barrier valve device) and is disposed around more than 50% of the outer surface 521 of the sleeve 422. This provides a mechanism for moving the sleeve 420 from its first configuration to its second configuration. However, alternative embodiments can include a single wire member that is disposed around more than 75% of the outer surface of the sleeve or that is disposed around more than 100% of the outer surface of the sleeve. For example, the wire member can be positioned such that it extends at least one full revolution around the outer surface of the sleeve.

As the actuator 418 is moved from its first position to its second position, the first wire member 422 is moved from its first configuration to its second configuration and is pulled through the loop 574, which moves the sleeve 420 from its first configuration to its second configuration. FIGS. 16 and 17 illustrate the sleeve 420 in the first configuration and the first wire member 422 in the first configuration.

Figure 18:
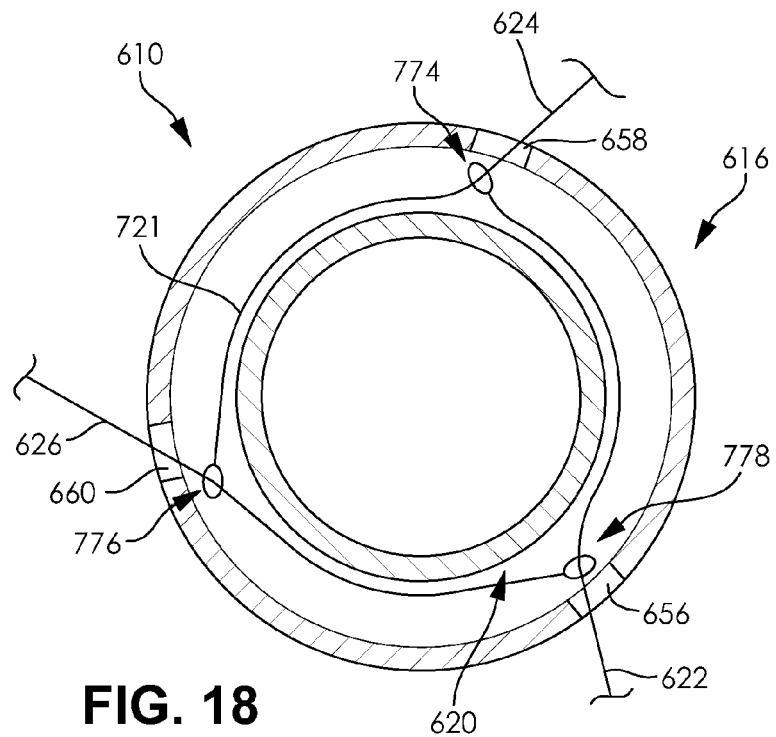
FIG. 18 is a sectional view of another example selective fluid barrier valve device taken along an axis that is orthogonal to the lengthwise axis of the selective fluid barrier valve device. The selective fluid barrier valve device is illustrated in a first configuration. Each of the actuator and the connector has been omitted for clarity.
Figure 19:
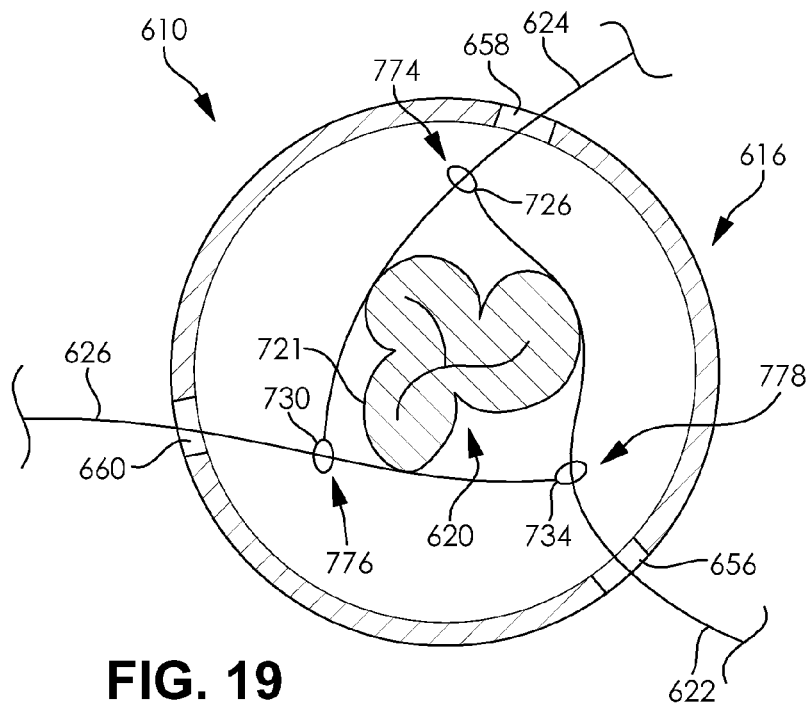
FIG. 19 is another sectional view of the selective fluid barrier valve device illustrated in FIG. 18 taken along an axis that is orthogonal to the lengthwise axis of the selective fluid barrier valve device. The selective fluid barrier valve device is illustrated in a second configuration.

FIGS. 18 and 19 illustrate another selective fluid barrier valve device 610. Selective fluid barrier valve device 610 is similar to the selective fluid barrier valve device 10 illustrated in FIGS. 1, 2, 3, 4, 5, 6, 7, 8A, 8B, 8C, 9A, 9B, 9C, 10A, 10B, and 10C and described above, except as detailed below. With respect to selective fluid barrier valve device 610, reference numbers in FIGS. 18 and 19 refer to the same structural element or feature referenced by the same number in FIGS. 1, 2, 3, 4, 5, 6, 7, 8A, 8B, 8C, 9A, 9B, 9C, 10A, 10B, and 10C, offset by 600. Thus, selective fluid barrier valve device 610 comprises a housing 616, an actuator (not shown), a sleeve 620, a first wire member 622, a second wire member 624, a third wire member 626, and a connector (not shown).

In the illustrated embodiment, the housing 616 omits the inclusion of a first cavity (e.g., first cavity 62), a second cavity (e.g., second cavity 64), and a third cavity (e.g., third cavity 66) and the first wire member 622, the second wire member 624, and third wire member 626 have a configuration as described below.

The first wire member 622 has a first end (not shown) attached to the actuator within the first cavity and a second end 726 attached to the first wire member 622 between the first end and the second end 726 of the first wire member 622. The first wire member 622 extends from the first end disposed within the first cavity defined by the actuator, through the first opening 656 defined by the housing 616, around a portion of the outer surface 721 of the sleeve 620, around the outer surface of the second wire member 624 and is attached to itself between the first end and the second end 726. Thus, the first wire member 622 defines a loop 774 at its second end 726 through which the second wire member 624 is disposed.

The second wire member 624 has a first end (not shown) attached to the actuator within the second cavity and a second end 730 attached to the second wire member 624 between the first end and the second end 730 of the second wire member 624. The second wire member 624 extends from the first end disposed within the second cavity defined by the actuator, through the second opening 658 defined by the housing 616, around a portion of the outer surface 721 of the sleeve 620, around the outer surface of the third wire member 626 and is attached to itself between the first end and the second end 730. Thus, the second wire member 624 defines a loop 776 at its second end 730 through which the third wire member 626 is disposed.

The third wire member 626 has a first end (not shown) attached to the actuator within the third cavity and a second end 734 attached to the third wire member 626 between the first end and the second end 734 of the third wire member 626. The third wire member 626 extends from the first end disposed within the third cavity defined by the actuator, through the third opening 660 defined by the housing 616, around a portion of the outer surface 721 of the sleeve 620, around the outer surface of the first wire member 622 and is attached to itself between the first end and the second end 734. Thus, the third wire member 626 defines a loop 778 at its second end 734 through which the first wire member 622 is disposed.

As the actuator is moved from its first position to its second position, each of the wire members 622, 624, 626 is moved from its first configuration to its second configuration. The first wire member 622 is pulled through the loop 778 defined by the third wire member 626 and the portion of the first wire member 622 that defines the loop 774 applies a force directed toward the first opening 656 on the second wire member 624. The second wire member 624 is pulled through the loop 774 defined by the first wire member 622 and the portion of the second wire member 624 that defines the loop 776 applies a force directed toward the second opening 658 on the third wire member 626. The third wire member 626 is pulled through the loop 776 defined by the second wire member 624 and the portion of the third wire member 626 that defines the loop 778 applies a force directed toward the third opening 660 on the first wire member 622. This configuration moves the sleeve 620 from its first configuration to its second configuration as the actuator is moved from its first position to its second position and each of the wire members 622, 624, 626 is moved from its first configuration to its second configuration. FIG. 18 illustrates the sleeve 620 in the first configuration and each of the wire members 622, 624, 626 in the first configuration. FIG. 19 illustrates the sleeve 620 in the second configuration and each of the wire members 622, 624, 626 in the second configuration.

Figures 20, 21, 22:
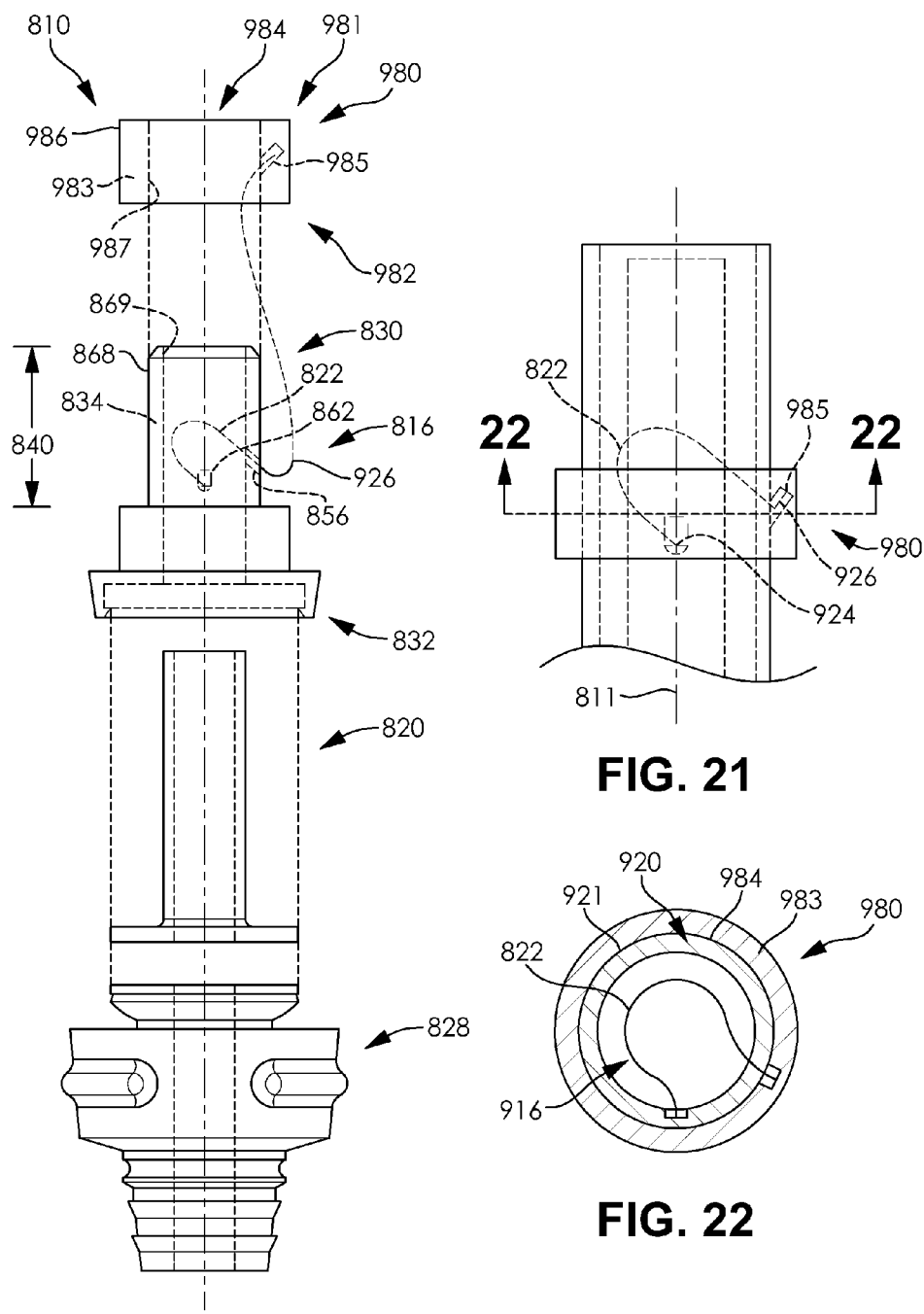
FIG. 20 is an exploded view of another example selective fluid barrier valve device.
FIG. 21 is a partial side view of the selective fluid barrier valve device illustrated in FIG. 20. The selective fluid barrier valve device is illustrated in a first configuration.
FIG. 22 is a cross-sectional view of the selective fluid barrier valve device illustrated in FIG. 21, taken along line 22-22. The sleeve has been omitted for clarity.

FIGS. 20, 21, and 22 illustrate another selective fluid barrier valve device 810. Selective fluid barrier valve device 810 is similar to the selective fluid barrier valve device 10 illustrated in FIGS. 1, 2, 3, 4, 5, 6, 7, 8A, 8B, 8C, 9A, 9B, 9C, 10A, 10B, and 10C and described above, except as detailed below. With respect to selective fluid barrier valve device 810, reference numbers in FIGS. 20, 21, and 22 refer to the same structural element or feature referenced by the same number in FIGS. 1, 2, 3, 4, 5, 6, 7, 8A, 8B, 8C, 9A, 9B, 9C, 10A, 10B, and 10C, offset by 800. Thus, selective fluid barrier valve device 810 comprises a housing 816, an actuator 818, a sleeve 820, a first wire member 822, and a connector 828.

In the illustrated embodiment, the actuator 818 of the selective fluid barrier valve device 810 is a slidable member 980 that is slidably disposed on the housing 816. The selective fluid barrier valve device 10 omits the inclusion of a second wire member (e.g., second wire member 24) and a third wire member (e.g., third wire member 26) and the housing 816 omits the inclusion of a groove (e.g., groove 50), a plurality of recesses (e.g., plurality of recesses 52), a second opening (e.g., second opening 58), a third opening (e.g., third opening 60), a second cavity (e.g., second cavity 64), and a third cavity (e.g., third cavity 66).

In the illustrated embodiment, the first opening 856 defined by the housing body 834 extends from the outer surface 868 of the housing 816 to the inner surface 869 of the housing 816 and toward the proximal end 830 of the housing 816. Thus, the first opening 856 has a lengthwise axis that is disposed at an angle relative to the lengthwise axis 811 of the selective fluid barrier valve device 810 (i.e., a plane that contains the lengthwise axis 811 of the selective fluid barrier valve device 810).

The actuator 818 is slidably disposed on the third portion 840 of the housing 816 and is moveable between a first position and a second position. In the first position, the actuator 818 is disposed a first distance from the proximal end 830 of the housing 816. In the second position, the actuator 818 is disposed a second distance from the proximal end 830 of the housing 816. The first distance is greater than the second distance such that axial movement of the actuator 818 toward the proximal end 830 of the housing 816 moves the sleeve 820 from its first configuration to the second configuration. Alternatively, an actuator can be positioned on a selective fluid barrier valve device such that it is slidably disposed on the third portion of a housing and is moveable between a first position and a second position. In the first position, the actuator is disposed a first distance from the proximal end of the housing. In the second position, the actuator is disposed a second distance from the proximal end of the housing. The first distance is less than the second distance such that axial movement of the actuator toward the distal end of the housing moves the sleeve from its first configuration to the second configuration The actuator 818 comprises a proximal end 981, a distal end 982, and an actuator body 983 that defines a passageway 984, a cavity 985, an outer surface 986, and an inner surface 987. The passageway 984 extends through the actuator 818 from the proximal end 981 to the distal end 982 of the actuator 818. The cavity 985 extends from an opening on the inner surface 987 toward the outer surface 986 and toward the proximal end 981 of the actuator 818. Thus, the cavity 985 has a lengthwise axis that is disposed at an angle relative to the lengthwise axis 811 of the selective fluid barrier valve device 810 (i.e., a plane that contains the lengthwise axis 811 of the selective fluid barrier valve device 810).

The first wire member 822 has a first end 924 attached to the housing 816 within the cavity 862 and a second end 926 attached to the actuator 818 within the cavity 985. The first wire member 822 extends from the first end 924 disposed within the cavity 862 defined by the housing 816, around the outer surface 921 of the sleeve 820, through the first opening 856 defined by the housing 816, to the second end 926 disposed within the cavity 985 defined by the actuator 818.

As the actuator 818 is moved from its first position to its second position, the first wire member 822 moves from its first configuration to the second configuration. The first wire member 822 is pulled through the first opening 856 defined by the housing 816 and the second end 926 of the first wire member 822 is advanced toward the proximal end 830 of the housing 816. This advances the sleeve 820 from the first configuration in which the passageway 916 defined by the sleeve 820 is open and fluid can pass through the passageway 916 to the second configuration in which the passageway 916 defined by the sleeve 820 is closed and fluid is prevented from passing through the passageway 916.

Methods of treatment are described herein. While the methods described herein are shown and described as a series of acts, it is to be understood and appreciated that the methods are not limited by the order of acts described and illustrated, as some acts may in accordance with these methods, be omitted, be repeated, or occur in different orders and/or concurrently with other acts described herein.

Figure 23:
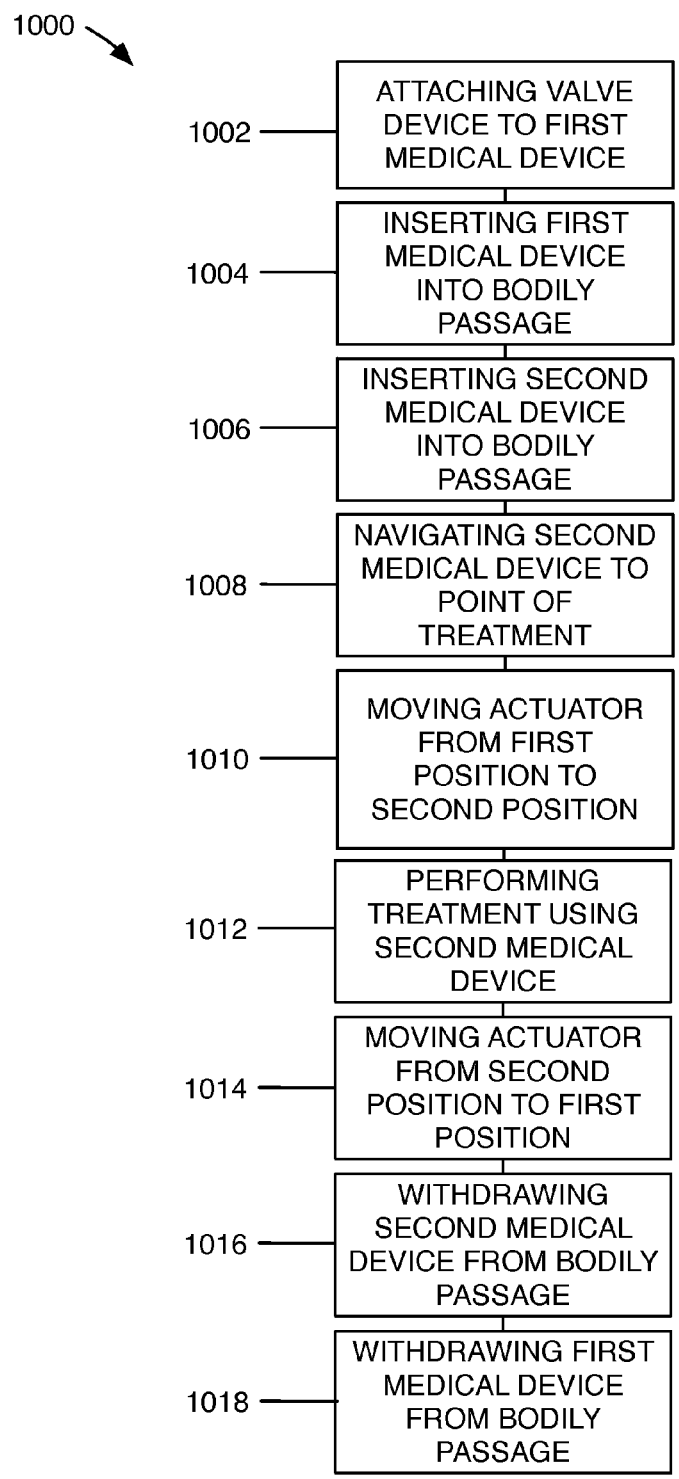
FIG. 23 is a flowchart representation of an example method of treatment.

FIG. 23 is a flowchart representation of a method of treatment 1000 using a selective fluid barrier valve device.

A step 1002 comprises attaching a selective fluid barrier valve device to a first medical device that has a proximal end, a distal end, and a body that defines a lumen that extends from the proximal end to the distal end. The selective fluid barrier valve device comprises a housing, an actuator, a sleeve, a first wire member, a second wire member, a third wire member, and a connector. Another step 1004 comprises inserting the first medical device into a bodily passage such that the distal end of the first medical device is disposed within the bodily passage. Another step 1006 comprises inserting a second medical device that has a proximal end and a distal end through the selective fluid barrier valve device and the first medical device such that the distal end of the second medical device is disposed within the bodily passage. Another step 1008 comprises navigating the distal end of the second medical device to a point of treatment within the bodily passage. Another step 1010 comprises moving the actuator from the first position to the second position. Another step 1012 comprises performing treatment using the second medical device. Another step 1014 comprises moving the actuator from the second position to the first position. Another step 1016 comprises withdrawing the second medical device from the bodily passage, the first medical device, and the selective fluid barrier valve device. Another step 1018 comprises withdrawing the first medical device from the bodily passage.

Step 1002 can be accomplished using any suitable selective fluid barrier valve device, and skilled artisans will be able to select a suitable selective fluid barrier valve device to use in a method of treatment according to a particular embodiment based on various considerations, including the type of treatment being performed. Example selective fluid barrier valve devices considered suitable to use in a method of treatment include the selective fluid barrier valve devices described herein, such as selective fluid barrier valve device 10, selective fluid barrier valve device 210, selective fluid barrier valve device 410, selective fluid barrier valve device 610, selective fluid barrier valve device 810, selective fluid barrier valve device 1110, variations thereof, and any other selective fluid barrier valve device considered suitable for a particular method of treatment. An exemplary selective fluid barrier valve device that can be used to accomplish the methods, steps, alternative steps, and/or optional steps described herein is illustrated and described with respect to FIGS. 1, 2, 3, 4, 5, 6, 7, 8A, 8B, 8C, 9A, 9B, 9C, 10A, 10B, and 10C, and comprises a housing 16, an actuator 18, a sleeve 20, a first wire member 22, a second wire member 24, a third wire member 26, and a connector 28. The selective fluid barrier valve device 10 is moveable between a first configuration and a second configuration, as described herein.

Step 1002 can be accomplished using any suitable medical device, and skilled artisans will be able to select a suitable medical device to use in a method of treatment according to a particular embodiment based on various considerations, including the type of treatment being performed. Example medical devices considered suitable to use in a method of treatment include tubular members, sheaths, cannulas, wire guides, and any other medical device considered suitable for a particular method of treatment. Step 1002 can be accomplished using a medical device that has any suitable length, structural configuration, and that is formed of any suitable material.

Step 1002 can be accomplished in any suitable manner and using any suitable process and/or technique, such as by inserting the distal end 142 of the connector 28 into the lumen defined by the first medical device and applying a force on the connector 28 that is directed toward the first medical device and maintaining the position of the first medical device, applying a force on the first medical device that is directed toward the connector 28 and maintaining the position of the connector 28, or applying a force on the connector 28 that is directed toward the first medical device and concurrently applying a force on the first medical device that is directed toward the connector 28 until the first medical device and the connector are attached to one another and a sealed engagement is provided between the connector 28 and the medical device. Optionally, the first medical device can comprise a component of the selective fluid barrier valve device such that it is attached to the connector.

In embodiments in which the connector 28 is provided as a separate component, another step comprises attaching the connector 28 to the housing 16. This step can be accomplished in any suitable manner and using any suitable process and/or technique, such as by positioning the proximal end 140 of the connector 28 at the distal end 32 of the housing 16 and applying a force on the housing 16 that is directed toward the connector 28 and maintaining the position of the connector 28, by applying a force on the connector 28 that is directed toward the housing 16 and maintaining the position of the housing 16, or by applying a force on the housing 16 that is directed toward the connector 28 and concurrently applying a force on the connector 28 that is directed toward the housing 16.

Step 1004 can be accomplished in any suitable manner and using any suitable process and/or technique, such as by applying a force on the selective fluid barrier valve device 10 and/or the first medical device that is directed toward the bodily passage such that the distal end of the first medical device is disposed within the bodily passage.

An optional step that can be completed prior to step 1004 comprises introducing a wire guide having a wire guide proximal end and a wire guide distal end into a bodily passage such that the wire guide distal end is disposed within the bodily passage. This optional step can be accomplished in any suitable manner and using any suitable process and/or technique, such as by applying a force directed toward the bodily passage on any suitable portion of a wire guide such that the wire guide distal end is disposed within the bodily passage. This optional step can be accomplished using any suitable wire guide, formed of any suitable material, and having any suitable length, and skilled artisans will be able to select a suitable wire guide, material, and length for a wire guide according to a particular embodiment based on various considerations, including the bodily passage being treated.

Another optional step that can be completed comprises advancing the wire guide distal end to, or beyond, a point of treatment within the bodily passage. This optional step can be accomplished in any suitable manner and using any suitable process and/or technique, such as by applying a force directed toward the bodily passage on any suitable portion of the wire guide such that the wire guide distal end is advanced distal to, or beyond, the point of treatment. Alternatively, a wire guide can be advanced proximal to, or to, a point of treatment. This step can be accomplished in any suitable manner and using any suitable process and/or technique, such as with the assistance of direct visualization of the wire guide (e.g., scope), transcutaneously, using an illuminated wire guide, a camera, or any other suitable visualization technique or through tactile feedback provided by the body of the ventilation tube.

In embodiments in which a wire guide is being used, an alternative to step 1004 comprises advancing the wire guide through the lumen defined by the first medical device and through the passageway defined by the sleeve and inserting the first medical device into a bodily passage such that the distal end of the first medical device is disposed within the bodily passage. This optional step can be accomplished in any suitable manner and using any suitable process and/or technique, such as by inserting the wire guide proximal end into and through the lumen defined by the first medical device and the passageway defined by the sleeve and applying a force directed toward the bodily passage on any suitable portion of the selective fluid barrier valve device 10.

An optional step that can be completed subsequent to step 1004 comprises navigating the distal end of the first medical device to a point of treatment within the bodily passage. This optional step can be accomplished in any suitable manner and using any suitable process and/or technique, such as by applying a force on the selective fluid barrier valve device 10 and/or the first medical device that is directed toward the bodily passage.

Step 1006 can be accomplished in any suitable manner and using any suitable process and/or technique, such as by applying a force on the second medical device directed toward the bodily passage and by inserting the distal end of the second medical device through the passageway 152 defined by the connector 28, through the passageway 116 defined by the sleeve 20, and through the lumen defined by the first medical device until the distal end of the second medical device is disposed within the bodily passage. Step 1006 can be accomplished using any medical device, and skilled artisans will be able to select a suitable medical device to use in a method of treatment according to a particular embodiment based on various considerations, including the type of treatment being performed. Example medical devices considered suitable to pass through a selective fluid barrier valve device and to use in a method of treatment include catheters, balloon catheters, suction devices, medical device delivery devices, wire guides, and any other medical device considered suitable for a particular method of treatment. Step 1006 can be accomplished using a medical device that has any suitable length, structural configuration, and that is formed of any suitable material.

An optional step that can be completed prior to step 1006 comprises withdrawing the wire guide. This optional step can be accomplished in any suitable manner and using any suitable process and/or technique, such as by applying a force directed away from the bodily passage on any suitable portion of the wire guide such that the wire guide is withdrawn from the bodily passage. Alternatively, if the second medical device is intended to be passed over the wire guide, an alternative to step 1006 comprises introducing the proximal end of the wire guide through a lumen defined by the second medical device and inserting the second medical device through the selective fluid barrier valve device and the first medical device such that the distal end of the second medical device is disposed within the bodily passage. This alternative step can be accomplished in any suitable manner and using any suitable process and/or technique, such as by inserting the wire guide proximal end into and through the lumen defined by the second medical device and applying a force directed toward the bodily passage on any suitable portion of the second medical device. The force directed toward the bodily passage is applied such that the distal end of the second medical device is advanced and passed through the passageway defined by the connector, through the passageway defined by the sleeve, and through the lumen defined by the first medical device and is disposed within the bodily passage.

Step 1008 can be accomplished in any suitable manner and using any suitable process and/or technique, such as by applying a force on the second medical device that is directed toward the bodily passage such that the distal end of the second medical device is disposed at the point of treatment within the bodily passage. Step 1008 is accomplished such that the distal end of the second medical device is disposed within the bodily passage at, or adjacent to, the point of treatment (e.g., the location in which treatment is intended to be performed).

Alternatively, step 1008 can be accomplished such that the distal end of the second medical device is disposed near, proximal to, or distal to a point of treatment within the bodily passage. An optional step that can be completed subsequent to, or during the completion of step 1008, comprises confirming the position of the distal end of the second medical device. This optional step can be accomplished using any suitable visualization technique. Example visualization techniques considered suitable include x-ray, fluoroscopy, ultrasound, direct visualization with a scope, magnetic resonance imaging, and any other visualization technique considered suitable for a particular embodiment.

An optional step comprises inserting a third medical device that has a proximal end and a distal end through the selective fluid barrier valve device and the first medical device such that the distal end of the third medical device is disposed within the bodily passage. This optional step can be accomplished in any suitable manner and using any suitable process and/or technique, such as by applying a force on the third medical device directed toward the bodily passage and by inserting the distal end of the third medical device through the passageway 152 defined by the connector 28, through the passageway 116 defined by the sleeve 20, and through the lumen defined by the first medical device until the distal end of the third medical device is disposed within the bodily passage. This optional step can be accomplished using any suitable medical device, such as those described herein. Any suitable number of medical device can be inserted through a selective fluid barrier valve device, such as one, at least one, two, a plurality, three, four, and any other number considered suitable for a particular method of treatment.

Another optional step comprises navigating the distal end of the third medical device to a point of treatment within the bodily passage. This optional step can be accomplished in any suitable manner and using any suitable process and/or technique, such as by applying a force on the third medical device directed toward the bodily passage such that the distal end of the third medical device is at, near, adjacent, distal to, or proximal to a point of treatment within the bodily passage.

Step 1010 can be accomplished in any suitable manner and using any suitable process and/or technique, such as by applying a rotational force on the actuator 18 while maintaining the position of the housing 16 such that the selective fluid barrier valve device 10 moves from the first configuration to the second configuration. When the selective fluid barrier valve device 10 is in the second configuration, the sleeve 20 is in the second configuration such that the inner surface 122 of the sleeve 20 contacts the outer surface of the second medical device and fluid is prevented from passing through the sleeve 20. When the sleeve 20 is in the second configuration, the second medical device is releasably attached to the sleeve 20 such that it cannot be withdrawn from the sleeve 20. With respect to the selective fluid barrier valve device 10, the rotational force is applied in clockwise direction about the lengthwise axis 11 of the selective fluid barrier valve device 10.

Alternatively, in embodiments in which a wire guide is disposed through the passageway 116 defined by the sleeve 20, when the sleeve 20 is in the second configuration, the inner surface 122 of the sleeve 20 will contact one or both of the wire guide and the second medical device and fluid is prevented from passing through the sleeve 20. When the sleeve 20 is in the second configured, the second medical device and the wire guide are releasably attached to the sleeve 20 such that the second medical device and the wire guide cannot be withdrawn from the sleeve 20.

In embodiments in which the selective fluid barrier valve device includes an actuator that is a slidable member, such as selective fluid barrier valve device 810, step 1010 can be accomplished in any suitable manner and using any suitable process and/or technique, such as by applying a force on the distal end of the actuator that is directed toward the proximal end of the housing while maintaining the position of the housing such that the selective fluid barrier valve device moves from the first configuration to the second configuration. When the selective fluid barrier valve device is in the second configuration, the sleeve is in the second configuration such that the inner surface of the sleeve contacts the outer surface of the second medical device and fluid is prevented from passing through the sleeve. When the sleeve is in the second configuration, the second medical device is releasably attached to the sleeve such that it cannot be withdrawn from the sleeve.

In embodiments in which the selective fluid barrier valve device includes a second actuator, such as selective fluid barrier valve device 1110 shown in FIGS. 24, 25, 26, and 27, step 1010 can be accomplished in any suitable manner and using any suitable process and/or technique, such as by applying a rotational force on the second actuator 1260 while maintaining the position of the housing 1116 such that the selective fluid barrier valve device 1110 moves from the first configuration to the second configuration. When the selective fluid barrier valve device 1110 is in the second configuration, the sleeve 1120 is in the second configuration such that the inner surface of the sleeve 1120 contacts the outer surface of the second medical device and fluid is prevented from passing through the sleeve 1120. When the sleeve 1120 is in the second configuration, the second medical device is releasably attached to the sleeve 1120 such that it cannot be withdrawn from the sleeve 1120. With respect to the selective fluid barrier valve device 1110, the rotational force is applied in clockwise direction about the lengthwise axis 1111 of the selective fluid barrier valve device 1110.

Step 1012 can be accomplished by performing any suitable treatment and will be based on the medical device passed through the selective fluid barrier valve device 10 and the lumen of the first medical device. Any suitable treatment can be performed and skilled artisans will be able to select a suitable treatment to perform according to a particular embodiment based on various considerations, including the medical device that has been inserted through the selective fluid barrier valve device and the lumen defined by the first medical device. An example treatment considered suitable to perform includes balloon angioplasty. However, any other suitable treatment can be performed.

Step 1014 can be accomplished in any suitable manner and using any suitable process and/or technique, such as by applying a rotational force on the actuator 18 while maintaining the position of the housing 16 such that the selective fluid barrier valve device 10 moves from the second configuration to the first configuration. When the selective fluid barrier valve device 10 is in the first configuration, the sleeve 20 is in the first configuration such that fluid can pass through the passageway 116 defined by the sleeve 20 and the second medical device can be withdrawn from the sleeve 20. With respect to the selective fluid barrier valve device 10, the rotational force is applied in counterclockwise direction about the lengthwise axis 11 of the selective fluid barrier valve device 10.

Alternatively, in embodiments in which a wire guide is disposed through the passageway 116 defined by the sleeve 20, when the sleeve 20 is in the first configuration, the second medical device and/or the wire guide can be withdrawn from the sleeve 20.

In embodiments in which the selective fluid barrier valve device includes an actuator that is a slidable member, such as selective fluid barrier valve device 810, step 1014 can be accomplished in any suitable manner and using any suitable process and/or technique, such as by applying a force on the proximal end of the slidable member that is directed toward the distal end of the housing while maintaining the position of the housing such that the selective fluid barrier valve device moves from the second configuration to the first configuration. When the selective fluid barrier valve device is in the first configuration, the sleeve is in the first configuration such that fluid can pass through the passageway defined by the sleeve and the second medical device can be withdrawn from the sleeve.

In embodiments in which the selective fluid barrier valve device includes a second actuator, such as selective fluid barrier valve device 1110 shown in FIGS. 24, 25, 26, and 27, step 1014 can be accomplished in any suitable manner and using any suitable process and/or technique, such as by applying a rotational force on the second actuator 1260 while maintaining the position of the housing 1116 such that the selective fluid barrier valve device 1110 moves from the second configuration to the first configuration. When the selective fluid barrier valve device 1110 is in the first configuration, the sleeve 1120 is in the first configuration such that fluid can pass through the passageway defined by the sleeve 1120 and the second medical device can be withdrawn from the sleeve 1120. With respect to the selective fluid barrier valve device 1110, the rotational force is applied in counterclockwise direction about the lengthwise axis 1111 of the selective fluid barrier valve device 1110.

Step 1016 can be accomplished in any suitable manner and using any suitable process and/or technique, such as by applying a force on the second medical device that is directed away from the bodily passage such that the second medical device is advanced proximally and is withdrawn from the first medical device, the selective fluid barrier valve device 10, and the bodily passage.

In embodiments in which a wire guide is disposed through the passageway 116 defined by the sleeve 20, an optional step comprises withdrawing the wire guide from the bodily passage and/or the selective fluid barrier valve device. This optional step can be accomplished in any suitable manner and using any suitable process and/or technique, such as by applying a force on the wire guide that is directed away from the bodily passage such that the wire guide is advanced proximally and is withdrawn from the bodily passage, the first medical device, and/or the selective fluid barrier valve device 10.

Step 1018 can be accomplished in any suitable manner and using any suitable process and/or technique, such as by applying a force on any suitable portion of the selective fluid barrier valve device 10 and/or the first medical device directed away from the bodily passage such that the first medical device is advanced proximally and is withdrawn from the bodily passage. Optionally, step 1018 can be accomplished in combination with step 1016. Optionally, in embodiments in which a wire guide is disposed within the passageway 116 defined by the sleeve 20, step 1018 can be accomplished in combination with the optional step of withdrawing the wire guide from the bodily passage.

An optional step comprises removing the selective fluid barrier valve device from the first medical device. This optional step can be accomplished in any suitable manner and using any suitable process and/or technique, such as by removing the distal end 142 of the connector 28 from the lumen defined by the first medical device by applying a force on the connector 28 that is directed away from the medical device while maintaining the position of the first medical device.

FIGS. 24, 25, 26, and 27 illustrate another selective fluid barrier valve device 1110. Selective fluid barrier valve device 1110 is similar to the selective fluid barrier valve device 10 illustrated in FIGS. 1, 2, 3, 4, 5, 6, 7, 8A, 8B, 8C, 9A, 9B, 9C, 10A, 10B, and 10C and described above, except as detailed below. With respect to selective fluid barrier valve device 1110, reference numbers in FIGS. 24, 25, 26, and 27 refer to the same structural element or feature referenced by the same number in FIGS. 1, 2, 3, 4, 5, 6, 7, 8A, 8B, 8C, 9A, 9B, 9C, 10A, 10B, and 10C, offset by 1100.

In the illustrated embodiment, the selective fluid barrier valve device 1110 comprises a housing 1116, a first actuator 1118, a sleeve 1120, a first wire member 1122, a second wire member 1124, a third wire member 1126, a connector 1128, and a second actuator 1260.

In the illustrated embodiment, the body 1174 of the first actuator 1118 defines a second plurality of recesses 1262 that extend about the circumference of the outer surface 1196 of the first actuator 1118 and a protuberance 1263. Each recess of the second plurality of recesses 1262 is disposed between the protuberance 1263 and the proximal end 1170 of the first actuator 1118. Each recess of the second plurality of recesses 1262 is cooperatively defined by a first wall 1264, a second wall 1266, and a base 1268. Each of the first wall 1264 and the second wall 1266 extends from the outer surface 1196 and toward the inner surface 1198 to the base 1268. The first wall 1264 is disposed at a first angle 1265 relative to a first portion of the base 1268. The second wall 1266 is disposed at a second angle 1267 relative to a second portion of the base 1268. The first angle 1265 is less than the second angle 1267. In the illustrated embodiment, the first angle 1265 is equal to 90 degrees and the second angle 1267 is greater than 90 degrees. Each recess of the second plurality of recesses 1262 is sized and configured to receive a projection of the plurality of projections 1280 defined by the second actuator 1260, as described below. The second plurality of recesses 1262 provide a mechanism for moving the selective fluid barrier valve device 1110 between the first configuration and the second configuration while preventing overtightening on any device or object disposed through the passageway 1216 defined by the sleeve 1120.

The protuberance 1263 extends from the outer surface 1196 away from the passageway 1178 defined by the first actuator 1118 and around the entire circumference of the outer surface 1196 of the first actuator 1118. However, alternative embodiments can include a protuberance that extends around a portion of the outer surface of a first actuator. The protuberance 1263 is sized and configured to be received by the groove 1278 defined by the second actuator 1260 such that when the protuberance 1263 is disposed within the groove 1278 the first actuator 1118 is moveably attached to the second actuator 1260 (e.g., a snap fit attachment between the first actuator 1118 and the second actuator 1260 is achieved).

While the first wall 1264 has been illustrated as being disposed at a first angle 1265 that is equal to 90 degrees relative to a first portion of the base 1268 and the second wall 1266 has been illustrated as being disposed at a second angle 1267 that is greater than 90 degrees relative to a second portion of the base 1268, a first wall and/or second wall can be disposed at any suitable angle relative to a base. Example angles considered suitable to position a first wall relative to a portion of a base include angles equal to, substantially equal to, or about 90 degrees, angles that are less than 90 degrees, angles that are greater than 90 degrees, angles that are acute, angles that are obtuse, and any other angle considered suitable for a particular embodiment. Example angles considered suitable to position a second wall relative to a portion of a base include angles equal to, substantially equal to, or about 135 degrees, angles that are less than 135 degrees, angles that are greater than 135 degrees, angles that are acute, angles that are obtuse, and any other angle considered suitable for a particular embodiment. Alternatively, a second wall of a recess can be complementary to the structural arrangement of a surface of a projection defined by a second actuator.

While a second plurality of recesses 1262 has been illustrated, alternative embodiments can include one or more projections such that each projection extends from the outer surface of an actuator and away from the inner surface. Each projection of the one or more projections can be cooperatively defined by a first wall, a second wall, and a top wall and sized and configured to be received a recess defined by a second actuator Each of the first wall and the second wall extends from the outer surface and away from the inner surface to the top wall. The first wall is disposed at a first angle relative to a first portion of the top wall. The second wall is disposed at a second angle relative to a second portion of the top wall. The first angle is less than the second angle. Example angles considered suitable to position a first wall relative to a portion of a top wall of a projection include angles equal to, substantially equal to, or about 90 degrees, angles that are less than 90 degrees, angles that are greater than 90 degrees, angles that are acute, angles that are obtuse, and any other angle considered suitable for a particular embodiment. Example angles considered suitable to position a second wall relative to a portion of a top wall of a projection include angles equal to, substantially equal to, or about 135 degrees, angles that are less than 135 degrees, angles that are greater than 135 degrees, angles that are acute, angles that are obtuse, and any other angle considered suitable for a particular embodiment. Alternatively, a second wall of a projection can be complementary to the structural arrangement of a surface of a projection defined by a second actuator.

While a second plurality of recesses 1262 has been illustrated as defined on the first actuator 1218, a selective fluid barrier valve device can include any suitable number of recesses defined at any suitable location on an actuator. Skilled artisans will be able to select a suitable number of recesses to define on an actuator and a suitable location to position each recess according to a particular embodiment based on various considerations, including the structural arrangement of an actuator of an embodiment. Example number of recesses considered suitable to include on an actuator include one, at least one, two, a plurality, three, four, five, six, seven, eight, nine, ten, eleven, twelve, and any other number considered suitable for a particular embodiment.

In the illustrated embodiment, the second actuator 1260 has a proximal end 1270, a distal end 1272, and a second actuator body 1274 that defines a passageway 1276, a groove 1278, a plurality of projections 1280, an outer surface 1282, and an inner surface 1284. The second actuator 1260 is movably attached to the first actuator 1118 and is moveable in a first direction 1271 and a second direction 1273, as shown in FIG. 26. Movement of the second actuator 1260 in the first direction 1271 moves the first actuator 1118 from its first position to its second position and movement of the second actuator 1260 in the second direction 1273 moves the first actuator 1118 from its second position to its first position.

In the illustrated embodiment, the second actuator 1260 is a rotatable member 1261 that can be rotated on the first actuator 1118 around the lengthwise axis 1111 of the selective fluid barrier valve device 1110. However, while a rotatable member 1261 has been illustrated, a selective fluid barrier valve device can include any suitable actuator capable of moving the selective fluid barrier valve device between a first configuration and a second configuration. Skilled artisans will be able to select a suitable actuator to include on a selective fluid barrier valve device according to a particular embodiment based on various considerations, including the number of wire members included in the selective fluid barrier valve device and/or the structural arrangement of a first actuator. Example actuators considered suitable to include on a selective fluid barrier valve device include rotatable actuators, linear actuators, slidable actuators, pivotable actuators, levers, and any other actuator considered suitable for a particular embodiment.

The passageway 1276 extends from an opening defined at the proximal end 1270 to an opening defined at the distal end 1272. The groove 1278 is defined on the inner surface 1284 of the second actuator 1260 between the distal end 1272 and the plurality of projections 1280. The groove 1278 extends into the second actuator housing 1274 from the inner surface 1284, away from the lengthwise axis 1111 of the selective fluid barrier valve device 1110, and around the entire circumference of the inner surface 1284 of the second actuator 1260. However, alternative embodiments can include a groove that extends about a portion of the circumference of the inner surface of an actuator. The groove 1278 is sized and configured to receive a portion of the first actuator 1118 (e.g., protuberance 1263). The distal end 1272 of the second actuator 1260 is sized and configured to be advanced distally over the protuberance 1263 defined by the first actuator 1118 such that the protuberance 1263 can be disposed within the groove 1278. The groove 1278 and the protuberance 1263 cooperatively provide a mechanism for moveably attaching the first actuator 1118 to the second actuator 1260 (e.g., snap fit configuration).

Each projection of the plurality of projections 1280 extends from the inner surface 1284 of the second actuator 1260, away from the outer surface 1282 of the second actuator 1260, and toward an axis that is offset from the lengthwise axis 1111 of the selective fluid barrier valve device 1110. In the illustrated embodiment, each projection of the plurality of projections 1280 has a surface 1286 that is curved. When the first actuator 1118 is assembled within the second actuator 1260, each projection of the plurality of projections 1280 extends from the inner surface 1284 of the second actuator 1260 and toward the first wall 1264 of a recess of the second plurality of recesses 1262.

Each projection of the plurality of projections 1280 is moveable between a first configuration, as shown in FIGS. 25 and 26, and a second configuration, as shown in FIG. 27, such that each projection is capable of deflecting as the second actuator 1260 is moved relative to the first actuator 1118. Each projection of the plurality of projections 1280 is biased to the first configuration and can be moved between its first configuration and second configuration in any suitable manner and using any suitable process and/or technique, such as by applying a first force on the surface 1286 of each projection of the plurality of projections 1280 directed toward the inner wall 1284. Movement of the first actuator 1118 from the first position to the second position can be accomplished in any suitable manner and using any suitable process and/or technique, such as by applying a rotational force to the second actuator 1260 in the first direction 1271 such that each projection of the plurality of projections 1280 applies a second force on the first actuator 1118 directed toward the second wall 1266. The second force required to move the first actuator 1118 to the second position is less than the first force required to deflect each projection of the plurality of projections 1280. Therefore, as the second actuator 1260 is moved in the first direction 1271, each projection of the plurality of projections 1280 advances along a base 1268 of a recess of the second plurality of recesses 1262 until it surface 1286 contacts the second wall 1266 of the recess and results in movement of the first actuator 1118. When the second actuator 1260 is moved in the first direction 1271 the first actuator 1118 moves from its first position to its second position such that the wire members 1122, 1124, 1126 interact with the sleeve 1120 and move the sleeve 1120 to its second configuration.

Movement of the first actuator 1118 from the second position to a third position (e.g., a position beyond that of the second position and in the first direction 1271, a position in which a device or component disposed within the passageway 1216 defined sleeve 1120 becomes damaged or overtightened by the sleeve 1120) can be accomplished in any suitable manner and using any suitable process and/or technique, such as by applying a rotational force to the second actuator 1260 in the first direction 1271 such that each projection of the plurality of projections 1280 applies a third force on the first actuator 1118 directed toward the second wall 1264. The third force required to move the first actuator 1118 to the third position is greater than the first force required to deflect each projection of the plurality of projections 1280. Therefore, when the first actuator 1118 is in the second position, as the second actuator 1260 is moved in the first direction 1271, each projection of the plurality of projections 1280 deflects to its second configuration such that the second actuator 1260 rotates relative to the first actuator 1118 and prevents the first actuator 1118 from moving to its third position. This arrangement prevents overtightening or damage to any device or component disposed through the passageway 1216 defined by the sleeve 1120.

Movement of the first actuator 1118 from the second position to the first position can be accomplished in any suitable manner and using any suitable process and/or technique, such as by applying a rotational force to the second actuator 1260 in the second direction 1273 such that each projection of the plurality of projections 1280 applies a fourth force on the first actuator 1118 directed toward the first wall 1264. Due to the structural configuration of the first wall 1264 relative to each projection of the plurality of projections 1280, the fourth force need only be greater than the force required to move each of the ribs 1184, 1186, 1188 from its respective recess of the plurality of recesses 1152 to another, different, recess of the plurality of recesses 1152. As the second actuator 1260 is moved in the second direction 1271, each projection of the plurality of projections 1280 advances along a base 1268 of a recess of the second plurality of recesses 1262 until it contacts the first wall 1264 of the recess and results in movement of the first actuator 1118. When the second actuator 1260 is moved in the second direction 1273 the first actuator 1118 moves from its second position to its first position such that the wire members 1122, 1124, 1126 interact with the sleeve 1120 and move the sleeve 1120 to its first configuration.

While a plurality of projections 1280 has been illustrated, a selective fluid barrier valve device can include any suitable number of projections defined at any suitable location on an actuator. Skilled artisans will be able to select a suitable number of projections to define on an actuator and a suitable location to position each projection according to a particular embodiment based on various considerations, including the structural arrangement of a first actuator of an embodiment. Example number of projections considered suitable to include on an actuator include one, at least one, two, a plurality, three, four, five, six, and any other number considered suitable for a particular embodiment.

While each projection of the plurality of projections 1280 has been illustrated as having a curved surface 1286, a projection defined by an actuator can have any suitable structural arrangement. Example structural arrangements considered suitable for a surface of a projection defined by an actuator and directed toward a second wall of a recess or projection defined by another actuator include surfaces that are curved, planar, multifaceted, and any other structural arrangement considered suitable for a particular embodiment.

While the first actuator 1118 and the second actuator 1260 have been illustrated as having particular structural arrangements, an actuator can have any suitable structural arrangement and can be based on various considerations, including the number of recesses and/or projections defined by an actuator included in a selective fluid barrier valve device. For example, while a protuberance has been illustrated as being defined by a first actuator and a groove has been illustrated as being defined by a second actuator, a first actuator can define a groove and a second actuator can define a protuberance. In addition, while the plurality of projections 1280 have been illustrated as extending away from the outer surface 1282 of the second actuator 1260, a plurality of projections defined by an actuator can have any suitable structural arrangement. For example, alternative embodiments can include one or more projections that have a structural arrangement similar to a rib, such as the ribs 84, 86, 88 illustrated with respect to FIGS. 1, 2, 3, 4, and 5, one or more recesses that have a structural arrangement similar to a recess, such as the plurality of recesses 52 illustrated with respect to FIGS. 2, 3, and 6, and/or a second actuator that defines a plurality of recesses defined along the inner surface of the second actuator (e.g., similar to the second plurality of recesses 1262) such that each recess is sized and configured to receive a deflectable projection defined by a first actuator (e.g., similar to the plurality of projections 1280).

Example—Analysis of Materials that can be Used to Form a Sleeve

| Material of Sleeve | Empty Sleeve Passageway | 0.018"Wire disposed within sleeve passageway | 0.035" Wire disposed within sleeve passageway | 14 French dilator disposed within sleeve passageway | Rating: |
|---|---|---|---|---|---|
| 80% - 4755 20% - 4765 | 3 g | 5.4 g | 50 g | 4.9 g | + |
| 100% - 4755 | 14.3 g | 2.8 g | 25.4 g | 11 g | + |
| 90% - 4755 10% - 4014 | 0 | 0 | 1.4 g | 0 | ++ |
| 80% - 4755 20% - 4014 | 0 | 0 | 0 | 0 | ++++ |
| 70% - 4755 30% - 4014 | 0 | 0 | 0 | 0 | ++++ |
| 60% - 4755 40% - 4014 | 0 | 0 | Trace | 0 | +++ |

Discussion

A quantitative analysis was performed on six (6) sleeves. The materials used to form the sleeves that were analyzed were off the shelf NuSil MED-4755, NuSil MED-4765, and NuSil MED-4014 in the proportions indicated in the table. Each sleeve was included in a selective fluid barrier valve device that was constructed to be similar to the embodiment illustrated in FIGS. 1, 2, 3, 4, 5, 6, 7, 8A, 8B, 8C, 9A, 9B, 9C, 10A, 10B, and 10C. The selective fluid barrier valve device was attached to a gravity flow rig and pressurized for 30 seconds per test at a pressure of 2.9 PSI+/−0.1 PSI (e.g., systolic pressure). Each sleeve was tested in the second configuration with no device disposed through the sleeve passageway and with the devices described in the table disposed through the sleeve passageway.

Results

Each of the sleeves tested was assigned a subjective qualitative rating between + and ++++ based on the performance of the sleeve during the analysis. Two out of the six (2/6) sleeves tested resulted in no leaks being detected in each test. Each of these sleeves was assigned a subjective qualitative rating of ++++. One out of the six (1/6) sleeves tested resulted in a trace leak being detected when a 0.035" wire was disposed within the sleeve passageway. This sleeve was assigned a subjective qualitative rating of +++. One out of the six (1/6) sleeves tested resulted in a leak being detected when a 0.035" wire was disposed in the sleeve passageway. This sleeve was assigned a subjective qualitative rating of ++. Two out of the six (2/6) sleeves tested resulted in leaks being detected in each test. Each of these sleeves was assigned a subjective qualitative rating of +.

As illustrated by the table, a sleeve formed of between about 70% and 80% of NuSil MED-4755 and between about 20% and 30% of NuSil MED-4014 is considered suitable for inclusion in a selective fluid barrier valve device. For example, a sleeve formed of about 80% of NuSil MED-4755 and about 20% of NuSil MED-4014 is considered suitable for inclusion in a selective fluid barrier valve device. Alternatively, a sleeve formed of about 70% of NuSil MED-4755 and about 30% of NuSil MED-4014 is considered suitable for inclusion in a selective fluid barrier valve device.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A selective fluid barrier valve device having a lengthwise axis and comprising:
   a housing having a housing proximal end, a housing distal end, and a housing body defining a housing passageway and a first opening, the housing passageway extending through the housing, the first opening extending through the housing body and providing access to the housing passageway;
   an actuator moveably attached to the housing and moveable between a first position and a second position;
   a sleeve disposed within the housing passageway and having a sleeve proximal end, a sleeve distal end, and a sleeve body defining a sleeve passageway extending through the sleeve, the sleeve moveable between a first configuration in which the sleeve passageway is open such that fluid can pass through the sleeve passageway and a second configuration in which the sleeve passageway is closed preventing fluid from passing through the sleeve passageway; and
   a first wire member having a first wire member first end attached to the housing and a first wire member second end attached to the actuator, the first wire member extending between the housing and the sleeve and through the first opening defined by the housing;
   wherein the sleeve is in the first configuration and the sleeve proximal end is disposed a first distance from the housing proximal end when the actuator is in the first position;
   wherein the sleeve is in the second configuration and the sleeve proximal end is disposed a second distance from the housing proximal end when the actuator is in the second position;
   wherein the second distance is different than the first distance;
   wherein the actuator has an actuator outer surface and an actuator inner surface;
   wherein the actuator body defines an actuator cavity extending from the actuator inner surface toward the actuator outer surface, the actuator cavity having a lengthwise axis that is parallel to said lengthwise axis of said selective fluid barrier valve device; and
   wherein the first wire member second end is disposed within the actuator cavity.

2. A selective fluid barrier valve device having a lengthwise axis and comprising:
   a housing having a housing proximal end, a housing distal end, and a housing body defining a housing passageway and a first opening, the housing passageway extending through the housing, the first opening extending through the housing body and providing access to the housing passageway;
   an actuator moveably attached to the housing and moveable between a first position and a second position;
   a sleeve disposed within the housing passageway and having a sleeve proximal end, a sleeve distal end, and a sleeve body defining a sleeve passageway extending through the sleeve, the sleeve moveable between a first configuration in which the sleeve passageway is open such that fluid can pass through the sleeve passageway and a second configuration in which the sleeve passageway is closed preventing fluid from passing through the sleeve passageway; and
   a first wire member having a first wire member first end attached to the housing and a first wire member second end attached to the actuator, the first wire member extending between the housing and the sleeve and through the first opening defined by the housing;
   wherein the sleeve is in the first configuration and the sleeve proximal end is disposed a first distance from the housing proximal end when the actuator is in the first position;
   wherein the sleeve is in the second configuration and the sleeve proximal end is disposed a second distance from the housing proximal end when the actuator is in the second position;
   wherein the second distance is different than the first distance;
   wherein the housing body defines a plurality of grooves within the housing passageway;
   wherein the sleeve has a sleeve outer surface and a sleeve inner surface, the sleeve body defining a plurality of protuberances extending from the sleeve outer surface and away from the sleeve inner surface;
   wherein each protuberance of the plurality of protuberances defined by the sleeve body is sized and configured to be received by a groove of the plurality of grooves defined by the housing body; and
   wherein at least one of the protuberances of the plurality of protuberances defined by the sleeve body is disposed within a groove of the plurality of grooves defined by the housing body.

3. A selective fluid barrier valve device having a lengthwise axis and comprising:
   a housing having a housing proximal end, a housing distal end, and a housing body defining a housing passageway, a first opening, a second opening, and a third opening, the housing passageway extending through the housing, each of the first opening, the second opening, and the third opening extending through the housing body and providing access to the housing passageway;
   an actuator moveably attached to the housing and moveable between a first position and a second position;
   a sleeve disposed within the housing passageway and having a sleeve proximal end, a sleeve distal end, and a sleeve body defining a sleeve passageway extending through the sleeve, the sleeve moveable between a first configuration in which the sleeve passageway is open such that fluid can pass through the sleeve passageway and a second configuration in which the sleeve passageway is closed preventing fluid from passing through the sleeve passageway;

a first wire member having a first wire member first end attached to the housing and a first wire member second end attached to the actuator, the first wire member extending between the housing and the sleeve and through the first opening defined by the housing;

a second wire member having a second wire member first end attached to the housing and a second wire member second end attached to the actuator, the second wire member extending between the housing and the sleeve and through the second opening defined by the housing; and a third wire member having a third wire member first end attached to the housing and a third wire member second end attached to the actuator, the third wire member extending between the housing and the sleeve and through the third opening defined by the housing;

wherein the sleeve is in the first configuration and the sleeve proximal end is disposed a first distance from the housing proximal end when the actuator is in the first position;

wherein the sleeve is in the second configuration and the sleeve proximal end is disposed a second distance from the housing proximal end when the actuator is in the second position;

wherein the second distance is greater than the first distance;

wherein the actuator has an actuator outer surface and an actuator inner surface;

wherein the actuator body defines an actuator cavity extending from the actuator inner surface toward the actuator outer surface, the actuator cavity having a lengthwise axis that is parallel to said lengthwise axis of said selective fluid barrier valve device; and wherein the first wire member second end is disposed within the actuator cavity.

4. A selective fluid barrier valve device having a lengthwise axis and comprising:

a housing having a housing proximal end, a housing distal end, and a housing body defining a housing passageway, a first opening, a second opening, and a third opening, the housing passageway extending through the housing, each of the first opening, the second opening, and the third opening extending through the housing body and providing access to the housing passageway;

an actuator moveably attached to the housing and moveable between a first position and a second position;

a sleeve disposed within the housing passageway and having a sleeve proximal end, a sleeve distal end, and a sleeve body defining a sleeve passageway extending through the sleeve, the sleeve moveable between a first configuration in which the sleeve passageway is open such that fluid can pass through the sleeve passageway and a second configuration in which the sleeve passageway is closed preventing fluid from passing through the sleeve passageway;

a first wire member having a first wire member first end attached to the housing and a first wire member second end attached to the actuator, the first wire member extending between the housing and the sleeve and through the first opening defined by the housing;

a second wire member having a second wire member first end attached to the housing and a second wire member second end attached to the actuator, the second wire member extending between the housing and the sleeve and through the second opening defined by the housing; and a third wire member having a third wire member first end attached to the housing and a third wire member second end attached to the actuator, the third wire member extending between the housing and the sleeve and through the third opening defined by the housing;

wherein the sleeve is in the first configuration and the sleeve proximal end is disposed a first distance from the housing proximal end when the actuator is in the first position;

wherein the sleeve is in the second configuration and the sleeve proximal end is disposed a second distance from the housing proximal end when the actuator is in the second position;

wherein the second distance is greater than the first distance;

wherein the housing body defines a plurality of grooves within the housing passageway;

wherein the sleeve has a sleeve outer surface and a sleeve inner surface, the sleeve body defining a plurality of protuberances extending from the sleeve outer surface and away from the sleeve inner surface;

wherein each protuberance of the plurality of protuberances defined by the sleeve body is sized and configured to be received by a groove of the plurality of grooves defined by the housing body; and wherein at least one of the protuberances of the plurality of protuberances defined by the sleeve body is disposed within a groove of the plurality of grooves defined by the housing body.

* * * * *